(12) United States Patent
Sher et al.

(10) Patent No.: US 7,517,991 B2
(45) Date of Patent: Apr. 14, 2009

(54) N-SULFONYLPIPERIDINE CANNABINOID RECEPTOR 1 ANTAGONISTS

(75) Inventors: Philip M. Sher, Plainsboro, NJ (US); Gang Wu, Princeton, NJ (US); William R. Ewing, Yardley, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 364 days.

(21) Appl. No.: 11/247,492

(22) Filed: Oct. 11, 2005

(65) Prior Publication Data

US 2006/0079556 A1 Apr. 13, 2006

Related U.S. Application Data

(60) Provisional application No. 60/617,953, filed on Oct. 12, 2004.

(51) Int. Cl.
C07D 211/06 (2006.01)
A61K 31/445 (2006.01)
(52) U.S. Cl. .................................. 546/195; 514/317
(58) Field of Classification Search .................. 546/195; 514/317
See application file for complete search history.

(56) References Cited

U.S. PATENT DOCUMENTS

| 3,674,836 A | 7/1972 | Creger |
| 3,983,140 A | 9/1976 | Endo et al. |
| 4,027,009 A | 5/1977 | Grier et al. |
| 4,231,938 A | 11/1980 | Monaghan et al. |
| 4,346,227 A | 8/1982 | Terahara et al. |
| 4,379,785 A | 4/1983 | Weyer et al. |
| 4,448,784 A | 5/1984 | Glamkowski et al. |
| 4,450,171 A | 5/1984 | Hoffman et al. |
| 4,499,289 A | 2/1985 | Baran et al. |
| 4,613,610 A | 9/1986 | Wareing |
| 4,639,436 A | 1/1987 | Junge et al. |
| 4,647,576 A | 3/1987 | Hoefle et al. |
| 4,681,893 A | 7/1987 | Roth |
| 4,686,237 A | 8/1987 | Anderson |
| 4,759,923 A | 7/1988 | Buntin et al. |
| 4,871,721 A | 10/1989 | Biller |
| 4,904,769 A | 2/1990 | Rauenbusch |
| 4,924,024 A | 5/1990 | Biller |
| 5,006,530 A | 4/1991 | Angerbauer et al. |
| 5,011,930 A | 4/1991 | Fujikawa et al. |
| 5,177,080 A | 1/1993 | Angerbauer et al. |
| 5,260,440 A | 11/1993 | Hirai et al. |
| 5,273,995 A | 12/1993 | Roth |
| 5,354,772 A | 10/1994 | Kathawala |
| 5,385,929 A | 1/1995 | Bjorge et al. |
| 5,447,954 A | 9/1995 | Gribble et al. |
| 5,488,064 A | 1/1996 | Sher |
| 5,491,134 A | 2/1996 | Sher et al. |
| 5,506,219 A | 4/1996 | Robl |
| 5,541,204 A | 7/1996 | Sher et al. |
| 5,594,016 A | 1/1997 | Ueno et al. |
| 5,612,359 A | 3/1997 | Murugesan |
| 5,686,104 A | 11/1997 | Mills et al. |
| 5,691,322 A | 11/1997 | Robl |
| 5,698,527 A | 12/1997 | Kim |
| 5,712,396 A | 1/1998 | Magnin et al. |
| 5,753,675 A | 5/1998 | Wattanasin |
| 5,770,615 A | 6/1998 | Cheng et al. |
| 5,776,983 A | 7/1998 | Washburn et al. |
| 5,990,109 A | 11/1999 | Chen et al. |
| 6,013,648 A * | 1/2000 | Rinaldi et al. ............. 514/235.2 |
| 6,043,265 A | 3/2000 | Murugesan et al. |
| 6,184,231 B1 | 2/2001 | Hewawasam et al. |
| 6,414,002 B1 | 7/2002 | Cheng et al. |
| 6,635,626 B1 | 10/2003 | Barrish et al. |
| 2006/0079556 A1 | 4/2006 | Sher et al. |

FOREIGN PATENT DOCUMENTS

| DE | 19622222 A1 | 6/1996 |
| EP | 0 142 146 | 11/1984 |
| EP | 0 221 025 | 10/1986 |
| EP | 0 675 714 B1 | 12/1993 |
| EP | 0 818 448 B1 | 6/1997 |
| EP | 1 022 272 B1 | 10/1998 |
| FR | 2596393 | 4/1986 |

(Continued)

OTHER PUBLICATIONS

F.Z. Dorwald "Side Reactions in Organic Synthesis: A Guide to Successful Synthesis Design" 2005, Wiley-VCH Verlag GmbH & KGaA, Wienheim.*

(Continued)

*Primary Examiner*—Rita J Desai
*Assistant Examiner*—John Mabry
(74) *Attorney, Agent, or Firm*—Maureen S. Gibbons

(57) ABSTRACT

The present application describes compounds according to Formula I, wherein $R^1$, $R^2$, $R^3$, $R^4$, X and Y are described herein. Additionally, the present application describes pharmaceutical compositions comprising at least one compound according to Formula I and optionally one or more additional therapeutic agents. Finally, the present application describes methods of treatment using the compounds according to Formula I both alone and in combination with one or more additional therapeutic agents.

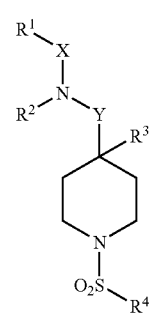

11 Claims, No Drawings

FOREIGN PATENT DOCUMENTS

| | | |
|---|---|---|
| GB | 2 205 837 A | 12/1988 |
| GB | 2 304 106 A | 3/1997 |
| WO | WO 86/03488 | 6/1986 |
| WO | WO 86/07054 | 12/1986 |
| WO | WO 94/15592 | 7/1994 |
| WO | WO 97/21993 | 6/1997 |
| WO | WO 97/35576 | 10/1997 |
| WO | WO 97/48701 | 12/1997 |
| WO | WO 99/00353 | 1/1999 |
| WO | WO 00/01389 | 1/2000 |
| WO | WO 00/15201 | 3/2000 |
| WO | WO 00/30665 | 6/2000 |
| WO | WO 00/38722 | 7/2000 |
| WO | WO 00/50574 | 8/2000 |
| WO | WO03/007888 | 1/2003 |
| WO | WO 03/042174 A1 | 5/2003 |

OTHER PUBLICATIONS

Database CAPLUS on STN (Columbus, OH, USA) No. 137:232912, "Preparation of azacycloalkyl- and arylsulfonylamino-substituted acetic acid derivatives as selective matrix-degrading metalloproteinase MMP-13 inhibitors useful as antiinflammatories" abstract, Fujimoto et al. (2002), see compounds delineated.

Database CAPLUS on STN (Columbus, OH, USA) No. 139:117342. "Preparation of biphenylsulfonamidoheterocycliclcarboxylates as metalloproteiase inhibitors" Pikul et al. (2003), see compounds delineated.

Database CAPLUS on STN (Columbus, OH, USA), No. 139:245903. "Prepartion of [(hetero) arylsulfonylamino]-[1-substituted-piperidin-4-yl]-acetic acids as metalloprotease inhibitors" Pikel et al., (2003), see compounds delineated.

Database CAPLUS on STN (Columbus, OH, USA) No. 137:216875, "Preparation of N-acyl-4-9heterocyclylaminomethyl) piperidines as NMDA/NR2B antagonists" Claiborne et al, (2002) see compounds delineated.

Database CAPLUS on STN (Columbus, OH, USA) No. 137:793427, "Preparation of N-substiuted nonaryl heterocyclyl amides as NMDA/NR2B antagonist for relieving pain" Liverton et al. (2002), see compound delineated.

Database CAPLUS on STN (Columbus, OH, USA) No. 138:90071 "Preparation of fluoropyrrolidinecarbonitrile derivatives as dipeptidyl peptidase inhibitors" abstract, Haffner et al. (2003) see compounds delineated.

Database CAPLUS on STN (Columbus, OH, USA) No. 140:217658, "Preparation of aminopyrimidinecarboxamides and their use as CB2-type cannabinoid receptor modulators" abstract, Eatherton et al. (Mar. 2004), see compound delineated.

Aranyos, A. et al., "Novel Electron-Rich Bulky Phosphine Ligands Facilitate the Palladium-Catalyzed Preparation of Diaryl Ethers", J. Am. Chem. Soc., vol. 121, pp. 4369-4378 (1999).

Avasimibe, "Treatment of Lipoprotein Disorders ACAT inhibitor", Drugs of the Future, vol. 24(1), pp. 9-15 (1999).

Biller, S. et al., "Squalene Synthase Inhibitors", Current Pharmaceutical Design, vol. 2, pp. 1-40 (1996).

Biller, S. et al., "Isoprenoid (Phosphinylmethyl) phosphonates as Inhibitors of Squalene Synthetase", J. of Medicinal Chemistry, vol. 31(10), pp. 1869-1871 (1988).

Corey, E.J. et al., "Application of Unreactive Analogs of Terpenoid Pyrophosphates to Studies of Multistep Biosynthesis. Demonstration that "Presqualene Pyrophosphate" Is an Essential Intermediate on the Path to Squalene", J. Amer. Chem. Soc., vol. 98(5), pp. 1291-1293 (1976).

Colombo, G., et al., "Appetite Suppression and Weight Loss after the Cannabinoid Antagonist SR 141716", Life Sciences, vol. 63(8), PL 113-117 (1998).

Di Marzo, V. et al., "Leptin-regulated endocannabinoids are involved in maintaining food intake", Nature, vol. 410, pp. 822-825 (2001).

Galiegue, S. et al., "Expression of central and peripheral cannabinoid receptors in human immune tissues and leukocyte subpopulations", Eur. J. Biochem., vol. 232, pp. 54-61 (1995).

Ghiselli, G., "The Pharmacological Profile of FCE 27677: A Novel ACAT Inhibitor with Potent Hypolipidemic Activity Mediated by Selective Suppression of the Hepatic Secretion of ApoB-100-Containing Lipoprotein", Cardiovascular Drug Reviews, vol. 16(1), pp. 16-30 (1998).

Glass, M. et al., "Cannabinoid Receptors in the Human Brain: A Detailed Anatomical and Quantitative Autoradiographic Study in the Fetal, Neonatal and Adult Human Brain", Neuroscience, vol. 77(2), pp. 299-318 (1997).

Hamann, B. et al., Sterically Hindered Chelating Alkyl Phosphines Provide Large Rate Accelerations in Palladium-Catalyzed Amination of Aryl Iodides, Bromides, and Chlorides, and the First Amination of Aryl Tosylates, J. Am. Chem. Soc., vol. 120, pp. 7369-7370 (1998).

Hara, S., "Ileal $Na^+$/bile acid cotransporter inhibitors", Drugs of the Future, vol. 24(4), pp. 425-430 (1999).

Hildebrandt, A. et al., "Antiobesity effects of chronic cannabinoid $CB_1$ receptor antagonist treatment in diet-induced obese mice", Eur. J. of Pharmacology, vol. 462, pp. 125-132 (2003).

Hollenbaugh, D. et al., "Cleavable CD40lg fusion proteins and the binding to sgp39", Journal of Immunological Methods, vol. 188, pp. 1-7 (1995).

Hollenbaugh, D. et al., "The human T Cell antigen gp39, a member of the TNF gene family, is a ligand for the CD40 receptor: expression of a soluble form of gp39 with B cell co-stimulatory activity", The EMBO Journal, vol. 11(12) pp. 4313-4321 (1992).

Ljung, B. et al., "AZ 242, a novel PPARα/γ agonist with beneficial effects on insulin resistance and carbohydrate and lipid metabolism in ob/ob mice and obese Zucker rats", Journal of Lipid Research, vol. 43, pp. 1855-1863 (2002).

Matsuda, L. et al., "Structure of a cannabinoid receptor and functional expression of the cloned cDNA", Nature, vol. 346, pp. 561-564 (1990).

McClard, R. et al., "Novel Phosphonylphosphinyl (P-C-P-C-) Analogues of Biochemically Interesting Diphosphates. Syntheses and Properties of P-C-P-C- Analogues of Isopentenyl Diphosphate and Dimethylallyl Diphosphate", J. Am. Chem. Soc., vol. 109, pp. 5544-5545 (1987).

Moreland, L. et al., "Treatment of Rheumatoid Arthritis with a Recombinant Human Tumor Necrosis Factor Receptor (p75)-Fc Fusion Protein", The New England Journal of Medicine, vol. 337(3), pp. 141-147 (1997).

Munro, S. et al., "Molecular characterization of a peripheral receptor for cannabinoids", Nature, vol. 365, pp. 61-65 (1993).

Nicolosi, R. et al., "The ACAT inhibitor, CI-1011 is effective in the prevention and regression of aortic fatty streak area in hamsters", Atherosclerosis, vol. 137, pp. 77-85 (1998).

Ortiz de Montellano, P. et al., "Inhibition of Squalene Synthetase by Farnesyl Pyrophosphate Analogues", Journal of Medicinal Chemistry, vol. 20(2) pp. 243-249 (1977).

Ravinet Trillou, C. et al., "Anti-obesity effect of SR141716, a CB1 receptor antagonist, in diet-induced obese mice", Am J Physiol Regul Integr Comp Physiol., vol. 284, pp. R345-R353 (2003).

Rosenblum, S. et al., "Discovery of 1-(4-Fluorophenyl)-(3R)-[3-(4-flurorphenyl)-(3S)-hydroxypropyl]-(4S)-(4-hydroxyphenyl)-2-azetidinone (SCH 58235): A Designed, Potent, Orally Active Inhibitor of Cholesterol Absorption", J. Med. Chem., vol. 41, pp. 973-980 (1998).

Rowland, N. et al., "Effects of the cannabinoid receptor antagonist SR 141716, alone and in combination with dexfenfluramine or naloxone, on food intake in rats", Psychopharmacology, vol. 159, pp. 111-116 (2001).

Salisbury, B. et al., "Hypocholesterolemic activity of a novel inhibitor of cholesterol absorption, SCH 48461", Atherosclerosis, vol. 115, pp. 45-63 (1995).

Smith, C. et al., "RP 73163: A Bioavailable Alkylsulphinyl-Diphenylimidazole ACAT Inhibitor[1]", Bioorganic & Medicinal Chemistry Letters, vol. 6(1), pp. 47-50 (1996).

Stout, David, "Inhibitors of Acyl-CoA: Cholesterol O-Acyl Transferase (ACAT) as Hypocholesterolemic Agents. 6. The First Water-Soluble ACAT Inhibitor with Lipid-Regulating Activity. Inhibitors of Acyl-CoA: Cholesterol Acyltransferase (ACAT). 7. Development of a Series of Substituted N-Phenyl-N-[(1-phenylcyclopentyl)-methyl]ureas with Enhanced Hypocholestrolemic Activity", Chemtracts-Organic Chemistry, vol. 8, pp. 359-362 (1995).

Williams, C. et al., "Anandamide induces overeating: mediation by central cannabinoid (CB1) receptors", Psychopharmacology, vol. 143, pp. 315-317 (1999).

Yajima, K. et al., "Combination therapy with PPARγ and PPARα agonists increases glucose-stimulated insulin secretion in db/db mice", Am. J. Physiol. Endocrinol. Metab., vol. 284, pp. E966-E971 (2003).

Sliskovic, D. et al., "ACAT Inhibitors: Potential Anti-atherosclerotic Agents", Current Medicinal Chemistry, vol. 1, pp. 204-225 (1994).

Krause, B. et al., "ACAT Inhibitors: Physiologic Mechanisms for Hypolipidemic and Anti-Atherosclerotic Activities in Experimental Animals", Inflammation:Mediators Pathways, pp. 173-198 (1995).

* cited by examiner

N-SULFONYLPIPERIDINE CANNABINOID RECEPTOR 1 ANTAGONISTS

RELATED APPLICATION

This application claims priority benefit under Title 35 § 119(e) of U.S. Provisional Application No. 60/617,953, filed Oct. 12, 2004, the contents of which are herein incorporated by reference.

BACKGROUND OF THE INVENTION

Delta-9-tetrahydrocannabinol or Delta-9 THC, the principle active component of *Cannabis sativa* (marijuana), is a member of a large family of lipophilic compounds (i.e., cannabinoids) that mediate physiological and psychotropic effects including regulation of appetite, immunosuppression, analgesia, inflammation, emesis, anti-nocioception, sedation, and intraocular pressure. Other members of the cannabinoid family include the endogenous (arachidonic acid-derived) ligands, anandamide, 2-arachidonyl glycerol, and 2-arachidonyl glycerol ether. Cannabinoids work through selective binding to and activation of G-protein coupled cannabinoid receptors. Two types of cannabinoid receptors have been cloned including CB-1 (L. A. Matsuda, et al., *Nature*, 346, 561-564 (1990)), and CB-2 (S. Munro, et al., *Nature*, 365, 61-65 (1993)). The CB-1 receptor is highly expressed in the central and peripheral nervous systems (M. Glass, et al., *Neuroscience*, 77, 299-318 (1997)), while the CB-2 receptor is highly expressed in immune tissue, particularly in spleen and tonsils. The CB-2 receptor is also expressed on other immune system cells, such as lymphoid cells (S. Galiegue, et al., *Eur J Biochem*, 232, 54-61 (1995)). Agonist activation of cannabinoid receptors results in inhibition of cAMP accumulation, stimulation of MAP kinase activity, and closure of calcium channels.

There exists substantial evidence that cannabinoids regulate appetitive behavior. Stimulation of CB-1 activity by anandamide or Delta-9 THC results in increased food intake and weight gain in multiple species including humans (Williams and Kirkham, *Psychopharm.*, 143, 315-317 (1999)). Genetic knock-out of CB-1 result in mice that were hypophagic and lean relative to wild-type litter mates (DiMarzo, et al., *Nature*, 410, 822-825 (2001)). Published studies with CB-1 small molecule antagonists have demonstrated decreased food intake and body weight in rats (Trillou, et. al., *Am. J. Physiol. Regal. Integr. Comp. Physiol.*, R345-R353, (2003)). Chronic administration of the CB-1 antagonist AM-251 for two weeks resulted in substantial body weight reduction and decreased adipose tissue mass (Hildebrandt, et. al., *Eur. J. Pharm*, 462, 125-132 (2003)). There are multiple studies that have assessed the anorexic effect of the Sanofi CB-1 antagonist, SR-141716 (Rowland, et. al., *Pyschopharm.*, 159, 111-116 (2001); Colombo, et. al., *Life Sci.*, 63, 113-117 (1998)). There are at least two CB-1 antagonists in clinical trials for regulation of appetite, Sanofi's SR-141716 and Solvay's SLV-319. Published Phase IIb data reveal that SR-141716 dose-dependently reduced body weight in human subjects over a 16 week trial period. CB-1 antagonists have also been shown to promote cessation of smoking behavior. Phase II clinical data on smoking cessation were presented in September of 2002 at Sanofi-Synthelabo's Information meeting. This data showed that 30.2% of patients treated with the highest dose of SR-141716 stayed abstinent from cigarette smoke relative to 14.8% for placebo.

DETAILED DESCRIPTION OF THE INVENTION

The present application describes compounds according to Formula I, pharmaceutical compositions comprising at least one compound according to Formula I and optionally one or more additional therapeutic agents and methods of treatment using the compounds according to Formula I both alone and in combination with one or more additional therapeutic agents.

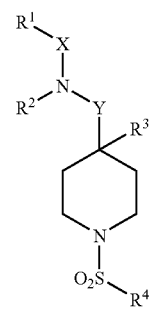

including all prodrugs, pharmaceutically acceptable salts and stereoisomers, wherein $R^1$, $R^2$, $R^3$, $R^4$, X and Y are described herein.

Definitions

The following definitions apply to the terms as used throughout this specification, unless otherwise limited in specific instances.

The term "alkyl" as employed herein, alone or as part of another group, includes saturated straight chain, branched chain, cyclic and bicyclic hydrocarbons, containing 1 to 20 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, cyclopropyl, cyclohexyl, norbornyl, and the like.

Unless otherwise indicated, the term "alkenyl" as used herein alone or as part of another group refers to straight chain, branched chain, cyclic and bicyclic hydrocarbons of 2 to 20 carbons, that include one or more double bonds, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, and 1-cyclohexenyl.

Unless otherwise indicated, the term "alkylidenyl" as used herein by itself or as part of another group refers to straight or branched chain geminally divalent radicals of 2 to 20 carbons, that are attached via a double bond, such as methylidenyl, isopropylidenyl, 1-pentylidenyl, and the like.

Unless otherwise indicated, the term "aryl" or "Ar" as employed herein alone or as part of another group refers to monocyclic and bicyclic aromatic groups containing 6 to 10 carbons in the ring portion (such as phenyl or naphthyl including 1-naphthyl and 2-naphthyl) and may optionally include one additional fused heterocyclic ring, for example:

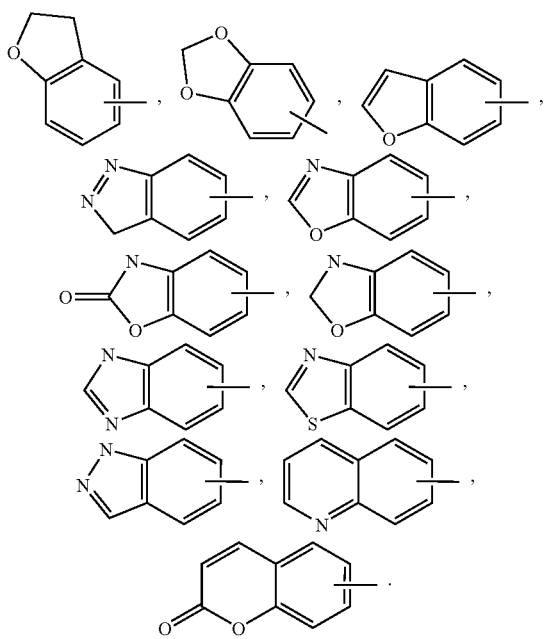

The term "arylalkyl" as used alone or as part of another group refers to an alkyl as defined herein, having an aryl substituent. Representative examples of arylalkyl include, but are not limited to, benzyl, 2-phenylethyl, 3-phenylpropyl, benzhydryl, naphthylmethyl, 4-trifluoromethylphenylpropyl and the like.

The term "halogen" or "halo" as used herein alone or as part of another group refers to chlorine, bromine, fluorine and iodine and also to pseudohalogen groups such as trifluoromethyl and difluoromethoxy.

Unless otherwise indicated, the term "alkoxy" or "aryloxy" as employed herein alone or as part of another group refers to an alkyl or aryl group, as defined herein, linked to an oxygen atom.

Unless otherwise indicated, the term "heteroaryl" as used herein alone or as part of another group refers to a 5- or 6-membered aromatic ring which includes 1, 2, 3 or 4 heteroatoms such as nitrogen, oxygen or sulfur, and includes possible N-oxides. Heteroaryl groups may also contain a fused benzene ring. Examples of heteroaryl groups include the following:

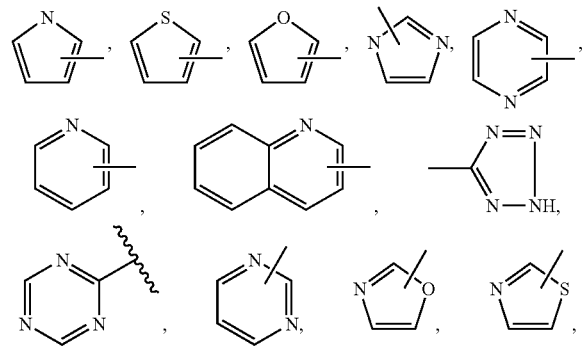

-continued

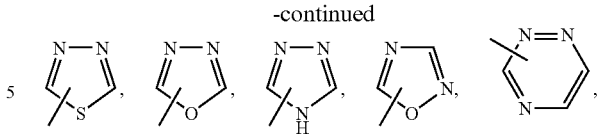

and the like.

Unless otherwise indicated, the term "heterocyclyl" as used herein alone or as part of another group refers to a 5- or 6-membered saturated ring which includes 1, 2, 3 or 4 heteroatoms such as nitrogen, oxygen or sulfur, and includes possible N-oxides. Examples of heterocyclyl groups include 4-morpholinyl, 3-piperidinyl, 2-tetrahydropyranyl, 3-tetrahydrothiophenyl, and the like.

As used herein, the term "heteroarylalkyl" means an alkyl group having a heteroaryl substituent.

It is understood that, where necessary, the valency of all atoms is made proper by the addition of hydrogens.

An administration of a therapeutic agent of the invention includes administration of a therapeutically effective amount of the agent of the invention. The term "therapeutically effective amount" as used herein refers to an amount of a therapeutic agent to treat or prevent a condition treatable by administration of a composition of the invention. That amount is the amount sufficient to exhibit a detectable therapeutic or preventative or ameliorative effect. The effect may include, for example, treatment or prevention of the conditions listed herein. The precise effective amount for a subject will depend upon the subject's size and health, the nature and extent of the condition being treated, recommendations of the treating physician, and the therapeutics or combination of therapeutics selected for administration. Thus, it is not useful to specify an exact effective amount in advance.

All stereoisomers of the compounds of the instant invention are contemplated, either in mixture or in pure or substantially pure form. The compounds of the present invention can have asymmetric centers at any of the carbon atoms including those within any of the R substituents. Consequently, compounds of formula I can exist in enantiomeric or diastereomeric forms or in mixtures thereof. The processes for preparation can utilize racemates, enantiomers or diastereomers as starting materials. In order to prepare diastereomeric or enantiomeric products, conventional methods for isomer separation may be employed. These include, for example, chromatographic techniques, chiral HPLC, fractional crystallization, and sequences of derivatization, separation and de-derivatization.

It is anticipated that compounds of formula I can be prepared as prodrugs by one skilled in the art, and the definitions of formula I above include all prodrug, stereoisomers, atropisomers and pharmaceutically acceptable salts of formulas I. Various forms of prodrugs are well known in the art. A comprehensive description of prodrugs and prodrug derivatives are described in:

a) *The Practice of Medicinal Chemistry*, Camille G. Wermuth et al., Ch 31, (Academic Press, 1996);

b) *Hydrolysis in Drug and Prodrug Metabolism*, Bernard Testa and Joachim M. Mayer, (Wiley-VCH, 2003);

c) *Design of Prodrugs*, edited by H. Bundgaard, (Elsevier, 1985); and d) *A Textbook of Drug Design and Development*, P. Krogsgaard-Larson and H. Bundgaard, eds. Ch 5, pgs 113-191 (Harwood Academic Publishers, 1991). Said references are incorporated herein by reference.

Any compound that can be converted in vivo to provide the bioactive agent (i.e., the compound of formula I) is a prodrug within the scope and spirit of the invention.

The compounds of formula I can be present as salts, which are also within the scope of this invention. Pharmaceutically acceptable (i.e., non-toxic, physiologically acceptable) salts are preferred. If the compounds of formula I have, for example, at least one basic center, they can form acid addition salts. These are formed, for example, with strong inorganic acids, such as mineral acids, for example sulfuric acid, phosphoric acid or a hydrohalic acid, with organic carboxylic acids, such as alkanecarboxylic acids of 1 to 8 carbon atoms which are unsubstituted or substituted, for example, by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or such as benzoic acid, or with organic sulfonic acids, such as ($C_1$-$C_4$) alkyl or arylsulfonic acids which are unsubstituted or substituted, for example by halogen, for example methyl- or p-toluene-sulfonic acid. Corresponding acid addition salts can also be formed having, if desired, an additionally present basic center. The compounds of formula I having at least one acid group (for example COOH) can form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono, di or tri-lower alkylamine, for example ethyl, tert-butyl, diethyl, diisopropyl, triethyl, tributyl or dimethylpropylamine, or a mono, di or trihydroxy lower alkylamine, for example mono, di or triethanolamine. Corresponding internal salts may furthermore be formed. Salts which are unsuitable for pharmaceutical uses, but which can be employed, for example, for the isolation or purification of free compounds of formula I or their pharmaceutically acceptable salts, are also included.

Preferred salts of the compounds of formula I which contain a basic group include monohydrochloride, hydrogen sulfate, methanesulfonate, phosphate, acetate and nitrate salts.

Preferred salts of the compounds of formula I which contain an acid group include sodium, potassium and magnesium salts and pharmaceutically acceptable organic amine salts.

The term "modulator" refers to a chemical compound with capacity to either enhance (e.g., "agonist" activity) or partially enhance (e.g., "partial agonist" activity) or inhibit (e.g., "antagonist" activity or inverse agonist activity) a functional property of biological activity or process (e.g., enzyme activity or receptor binding); such enhancement or inhibition may be contingent on the occurrence of a specific event, such as activation of a signal transduction pathway, and/or may be manifest only in particular cell types.

The present invention provides compounds of formula I, pharmaceutical compositions employing such compounds and methods of using such compounds. In particular, the present invention provides for a pharmaceutical composition comprising a therapeutically effective amount of a compound of formula I alone or in combination with a pharmaceutically acceptable carrier.

Further, in accordance with the present invention, a method is provided for preventing, inhibiting or treating the progression or onset of diseases or disorders associated with the cannabinoid receptor, such as the diseases or disorders defined above and hereinafter, wherein a therapeutically effective amount of a compound of formula I is administered to a mammalian, i.e., human patient in need of treatment.

The compounds of the invention can be used alone, in combination with other compounds of the present invention, or in combination with one or more other agent(s) active in the therapeutic areas described herein.

In addition, a method is provided for preventing, inhibiting or treating the diseases as defined above and hereinafter, wherein a therapeutically effective amount of a combination of a compound of formula I and another compound of the invention and/or another type of therapeutic agent, is administered to a mammalian patient in need of treatment.

Methods of Preparation

The following abbreviations are employed herein:
min=minute(s)
h=hour(s)
L=liter(s)
mL=milliliter(s)
μL=microliter(s)
g=gram(s)
mg=milligram(s)
mol=mole(s)
M=molar
mmol=millimole(s)
HPLC=high performance liquid chromatography
HPLC/MS or LC/MS=high performance liquid chromatography/mass spectrometry
MS or Mass Spec=mass spectrometry
[M+H]$^+$=parent plus a proton
[M+Na]$^+$=parent plus a sodium ion
[M−H]$^-$=parent minus a proton
Me=methyl
Et=ethyl
Ph=phenyl
TMS=trimethylsilyl
Ts=p-toluenesulfonyl
Ac=acetyl
THF=tetrahydrofuran
TFA=trifluoroacetic acid
EDC=1-[3-(dimethylamino)propyl]-3-ethylcarbodiimide hydrochloride
HOAt=1-hydroxy-7-azabenzotriazole
(BOC)$_2$O=di-tert-butyl dicarbonate
mCPBA=m-chloroperoxybenzoic acid
Ra—Ni=Raney® Nickel
LDA=lithium diisopropylethylamide
pyr=pyridine
DIBAl—H=diisobutylaluminum hydride The compounds of formula I of the invention can be prepared as shown below in the following reaction schemes and description thereof, as well as by using relevant published literature procedures that may be used by one skilled in the art. Exemplary reagents and procedures for these reactions appear hereinafter and in the working Examples.

Synthetic Schemes 1 to 13 below provide general synthetic routes for the synthesis of the compounds of formula I. The reaction steps are subject to the constraints noted. For example, a reaction step noted "for products wherein $R^3$ is H" is subject to the constraint that only products in which $R^3$ is hydrogen may be prepared.

In the synthetic schemes, Y' represents a bond in synthetic intermediates leading to compounds of formula I in which Y is —$CR^5R^6$—, and Y' represents —$CR^7R^8$— in synthetic intermediates leading to compounds of formula I in which Y is —$CR^5R^6CR^7R^8$—. For example, when the group $H_2NCO-Y'-$ is reduced to $H_2NCH_2-Y'-$, $-CH_2-$ maps to $-CR^5R^6-$ within Y, and Y' may be either a bond or $-CR^7R^8-$.

In the synthetic schemes, PG represents any standard nitrogen protecting group known to those skilled in the art—see Protective Groups in Organic Synthesis (2$^{nd}$ Edition, T. W. Greene and P. G. M. Wuts, John Wiley & Sons, 1991), especially t-butoxycarbonyl (BOC).

In the synthetic schemes, LG represents a leaving group, especially chloride, bromide, iodide, methanesulfonate, trifluoromethanesulfonate or p-toluenesulfonate which is useful in nucleophilic displacement and/or palladium catalyzed coupling reactions. LG may be acetate when bonded to a carbonyl as in acetic anhydride.

In the synthetic schemes, R (lacking a superscripted numeral) represents an alkyl, alkenyl or arylalkyl group.

In the synthetic schemes, M represents a monovalent metal atom or metal-centered group that renders nucleophilic the group to which it is attached. For example, M may be lithium as in butyllithium, chloromagnesium as in benzylmagnesium chloride, Cu(CN)Li as in $H_2C=CHCu(CN)Li$, etc.

SCHEME 1

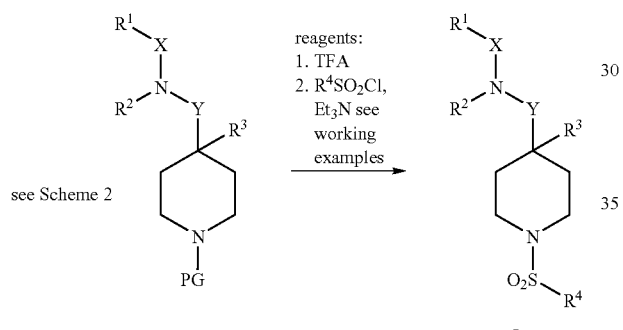

SCHEME 2

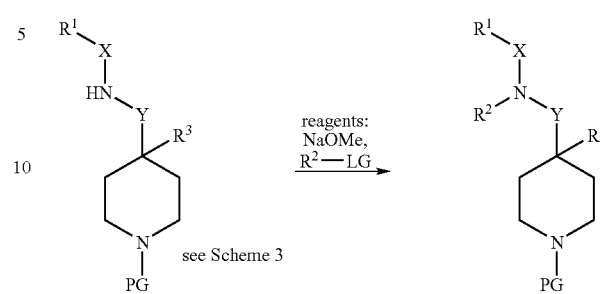

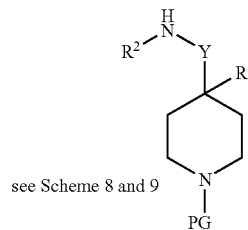

SCHEME 3

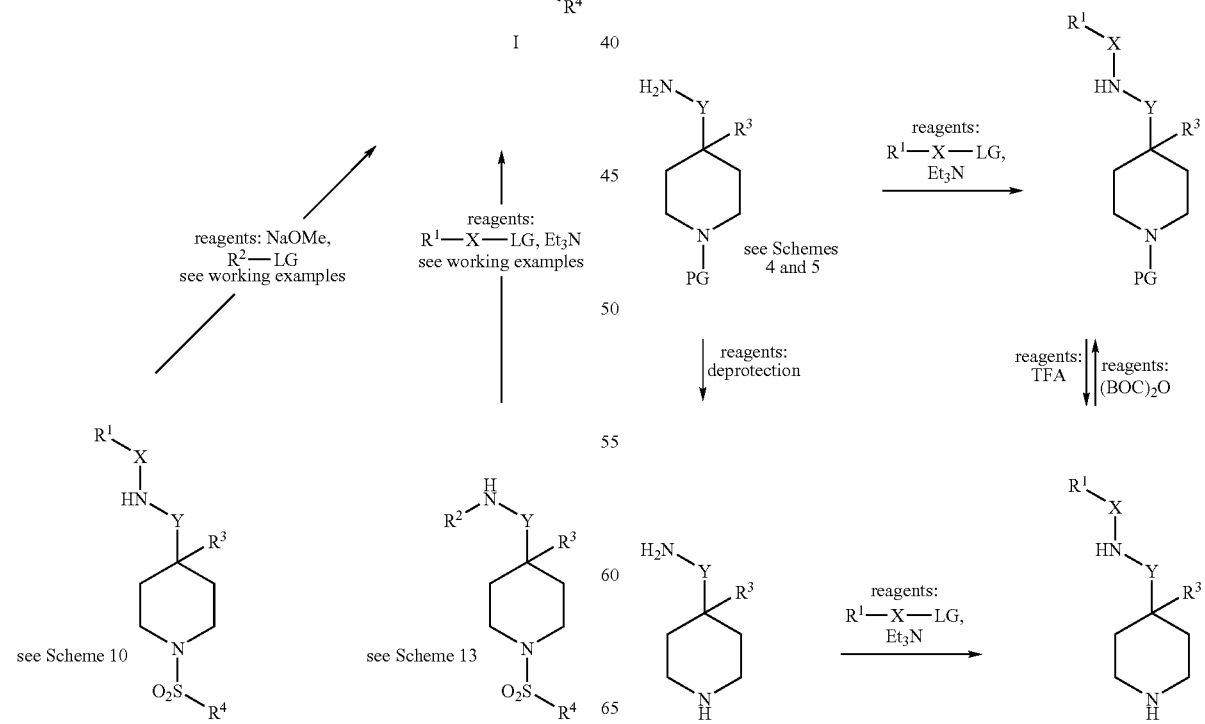

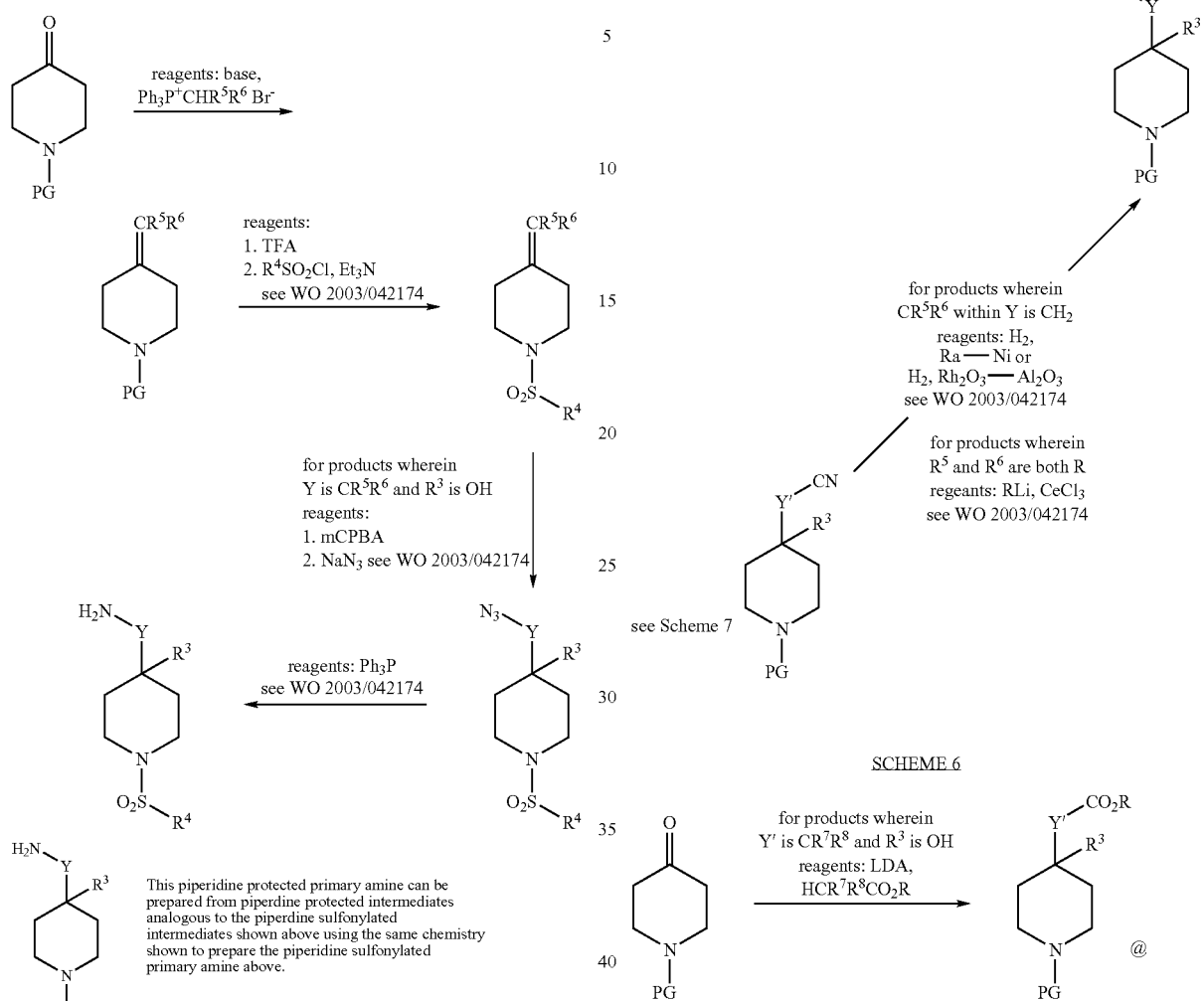
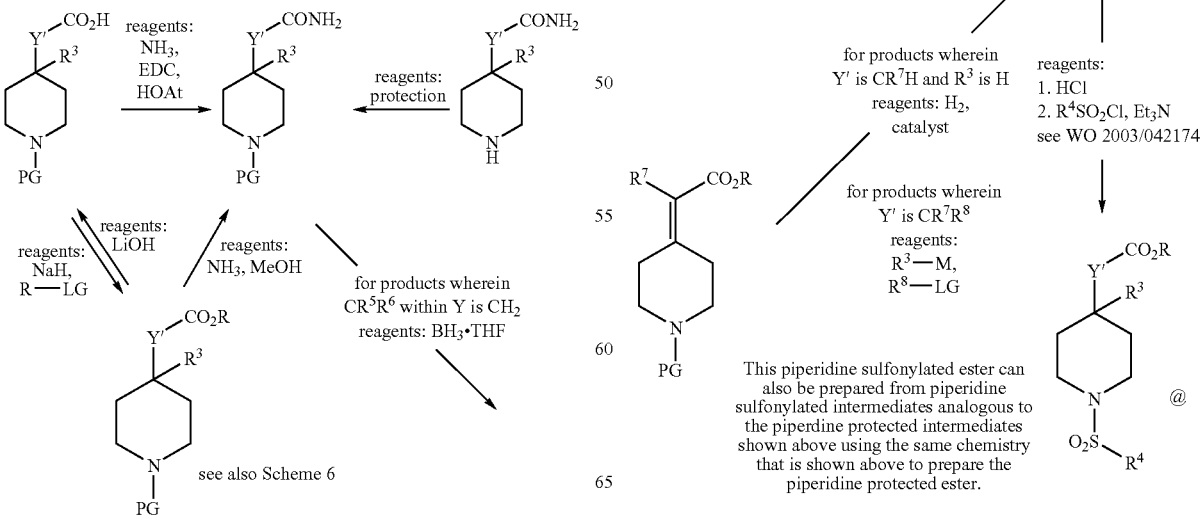

SCHEME 7
SCHEME 8
SCHEME 9
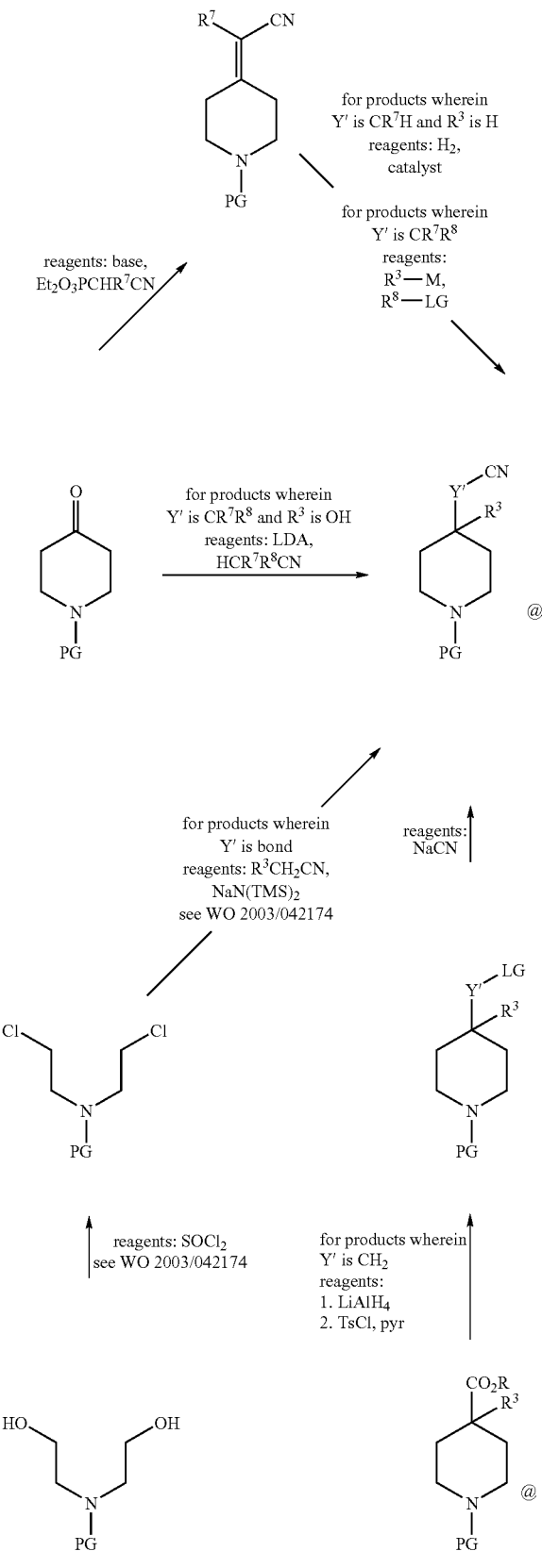
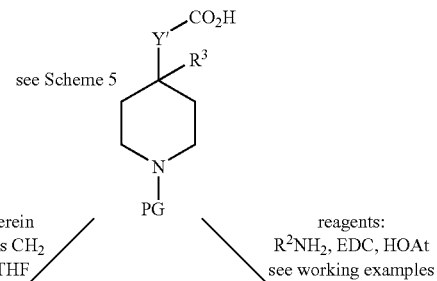
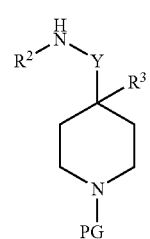

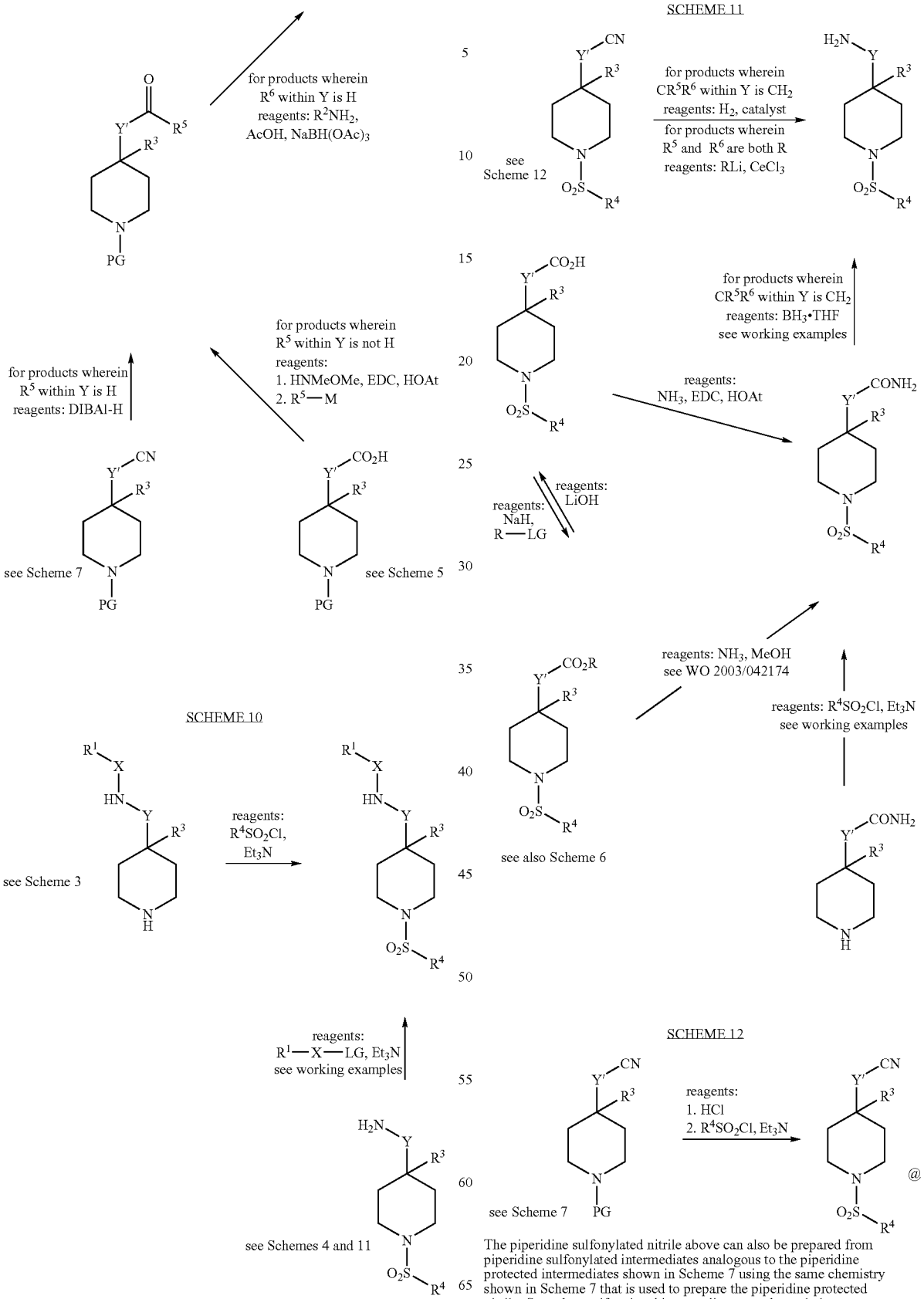

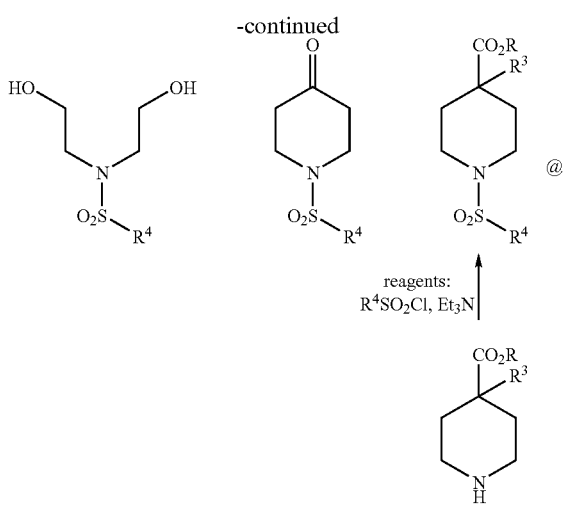

SCHEME 13

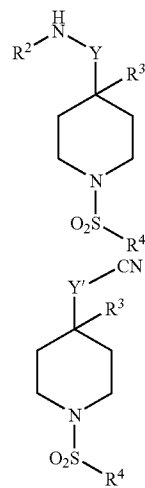

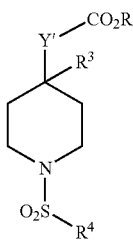

see Scheme 12

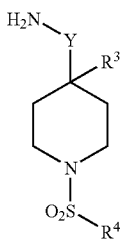

see Schemes 6 and 11 see Schemes 4 and 11

The secondary amine can be prepared from piperidine sulfonylated intermediates analogous to the piperidine protected intermediates shown in Schemes 8 and 9 using the same chemistry shown in Schemes 8 and 9 that is used to prepare the piperidine protected secondary amine. Some key piperidine sulfonylated intermediates are shown below.

In the synthetic schemes above the reagent lists are abbreviated. References cited provide full details and in some cases alternative reagents. It is understood that the reagents shown in the synthetic schemes are example reagents, not meant to be limiting. Those skilled in the art will recognize that there are many acids (hydrochloric acid, polyphosphoric acid, etc.), many bases (sodium hydride, potassium methoxide, etc.), many oxidants (hydrogen peroxide, 3-chloroperoxybenzoic acid, Dess-Martin periodinane, etc.), many hydrogenation catalysts (palladium, platinum oxide, Raney® Nickel, etc.), and so on that may be employed to synthesize the compounds of the invention. In some cases alternative reagents known to those skilled in the art will be superior to those listed in the synthetic schemes. Alternative reagents may be found in Reagents For Organic Synthesis (Fieser and Fieser, John Wiley & Sons) and Compendium of Organic Synthetic Methods (John Wiley & Sons). These references will also provide guidance in cases where the synthetic schemes designate only a class of reagent rather than a specific reagent (for example oxidant rather than hydrogen peroxide). In some instances the synthetic schemes refer not to specific reagents or reagent classes, but rather to name reactions, for example Birch reduction (sodium, liquid ammonia; used for reduction of benzene rings to 1,4-cyclohexadienes) and Curtius rearrangement (a. thionyl chloride b. sodium azide c. alkanol, heat; used for conversion of carboxyl groups to alkoxycarbonylamino groups). Name reactions and their experimental details are well-known to those skilled in the art (see Organic Syntheses Based on Name Reactions and Unnamed Reactions, A. Hassner and C. Stumer, Pergamon Press, 1994).

The references provided within the synthetic schemes are not intended to constrain the applicability of the reaction steps, but rather to exemplify the reactions and provide further experimental detail.

In the synthetic schemes, the substituents $R^5$ and $R^6$ are meant to have interchangeable meanings and to differ only as required by their relationship to one another. For example, if a particular reaction scheme shows the synthesis of an intermediate wherein $R^5$ is hydrogen and $R^6$ is an alkyl group, then it is equivalent to say that $R^5$ is the alkyl group and $R^6$ is hydrogen, but exactly one of the two must be hydrogen and the other must be an alkyl group. The choice of designating a substituent as $R^5$ or $R^6$ in the reaction schemes is generally arbitrary and is not meant to convey stereochemical information. Likewise, $R^7$ and $R^8$ are meant to have interchangeable meanings and to differ only as required by their relationship to one another.

In general, the interchange of functional groups within $R^1$, $R^2$, $R^3$, $R^4$, $R^5$, $R^6$, $R^7$ and $R^8$ may be accomplished according to the methods and procedures described in Compendium of Organic Synthetic Methods (John Wiley & Sons), Comprehensive Organic Functional Group Transformations (Editors A. R. Katritzky, O. Meth-Cohn and C. W. Rees, Pergamon Press) and Comprehensive Organic Transformations—A Guide To Functional Group Preparations (R. C. Larock, VCH Publishers, 1989). For example, a compound of formula I having a double bond in $R^2$ may be reduced by catalytic hydrogenation to produce a compound of formula I that is saturated in $R^2$. As another example, an intermediate in which $R^3$ is a hydroxyl group may be alkylated with benzyl bromide to produce an intermediate in which $R^3$ is a benzyloxy group. As another example, an intermediate in which $R^4$ is a bromophenyl group may undergo palladium catalyzed coupling with an arylboronic acid to produce an intermediate in which $R^4$ is a biphenyl.

Generally, compounds of formula I and synthetic intermediates in which $R^4$ or any other R group contains an aryl moiety substituted by cyano, alkyl, alkenyl, aryl, heteroaryl, arylalkyl, arylalkenyl, heteroarylalkyl, heteroarylalkenyl, alkoxy, aryloxy or any type of amino group may be prepared from the corresponding compounds of formula I and synthetic intermediates wherein the aryl moiety is substituted by halo or hydroxy, using various palladium catalyzed coupling procedures as described in Aranyos, et al., J. Am. Chem. Soc. 1999, 121, 4369-4378 and Hamann, et al., J. Am. Chem. Soc. 1998, 120, 7369-7370 and references contained therein, and in recent papers authored by Gregory C. Fu, Stephen L. Buchwald, or John F. Hartwig. These procedures are directly applicable when the aryl moiety is substituted by halo. When the aryl moiety is substituted by hydroxy, prior activation by conversion of the hydroxyl group to a trifluoromethylsulfonyloxy group, as described in the aforementioned references, is required.

It is understood that during the course of manipulating any functional group within $R^1$, $R^2$, $R^3$, $R^4$, $R^5$, $R^6$, $R^7$ and $R^8$ in compounds of formula I or at any stage of synthesis, standard protecting groups, as described in Protective Groups in Organic Synthesis (2$^{nd}$ Edition, T. W. Greene and P. G. M. Wuts, John Wiley & Sons, 1991), may be employed to avoid undesired reaction of any other functional group.

In the synthetic schemes, ester and nitrile intermediates marked with the symbol @ in which Y' is a bond or there is no Y', and R$^3$ is alkyl, alkenyl or arylalkenyl, may be prepared from the analogous intermediates marked with the symbol @ in which R$^3$ is hydrogen by treatment with a base such as lithium diisopropylethylamide and the appropriate electrophile, R$^3$-LG, in tetrahydrofuran, as described in WO 2003/042174. Ester and nitrile intermediates marked with the symbol @ in which Y' is CR$^7$R$^8$ and R$^7$ or R$^8$ is alkyl, alkenyl, arylalkyl or arylalkenyl may be prepared from the analogous intermediates marked with the symbol @ in which R$^7$ or R$^8$ is hydrogen by treatment with a base such as lithium diisopropylethylamide and the appropriate electrophile, R$^7$-LG or R$^8$-LG, in tetrahydrofuran.

EXAMPLES

The following Examples serve to better illustrate, but not limit, some of the preferred embodiments of the invention.

General

Reverse phase preparative HPLC separation employed an octadecyl sulfate (C-18) column eluting with a solvent gradient of solvents A and B, starting with 20% or more of solvent B and finishing with 100% of solvent B. Solvent A was 10% methanol in water, and solvent B was 90% methanol in water. In some cases both solvents A and B contained 0.1% of trifluoroacetic acid, as noted. Analytical HPLC/MS employed the same type of column and solvents A and B containing either 0.1% trifluoroacetic acid or 10 mM ammonium acetate. Reverse phase analytical HPLC employed the same type of column and solvents, except that the solvents contained 0.2% phosphoric acid.

Example 1

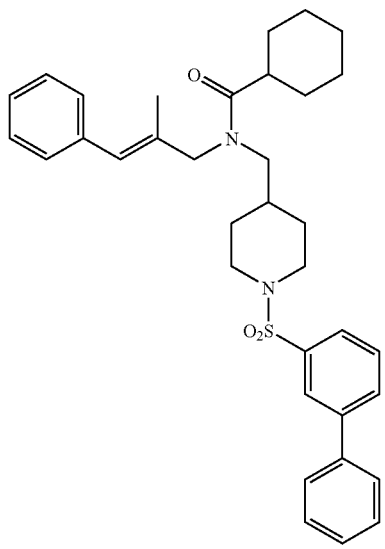

A mixture of 4-aminomethyl-1-t-butoxycarbonylpiperidine (3.6 g, 16.8 mmol), (E)-2-methyl-3-phenylpropenal (3.9 g, 26.7 mmol), acetic acid (3.9 g, 65 mmol), and 1,2-dichloroethane (30 mL) was stirred under argon at room temperature for 30 min before sodium triacetoxyborohydride (4.1 g, 19.3 mmol) was added. After 3 h saturated aqueous sodium bicarbonate was added to make the mixture basic, then it was diluted with water and extracted with dichloromethane (three times). The combined extracts were dried (anhydrous sodium sulfate) and evaporated under vacuum prior to column chromatography (silica gel, step-wise gradient of 2% to 4% of (10% concentrated aqueous ammonium hydroxide in methanol) in dichloromethane), which provided 4-(N-(2-methyl-3-phenyl-2-(E)-propenyl)aminomethyl)-1-t-butoxycarbonylpiperidine (3.72 g, 64% yield) as a pale yellow oil. A smaller excess of aldehyde over amine may produce optimal desired product yields when other aldehydes are used.

To a solution of 4-(N-(2-methyl-3-phenyl-2-(E)-propenyl)aminomethyl)-1-t-butoxycarbonylpiperidine (1.44 g, 4.18 mmol) and triethylamine (0.80 g, 7.9 mmol) in dichloromethane (60 mL) stirring at 0° C. under argon, was added cyclohexanecarbonyl chloride (0.75 g, 5.1 mmol) in a single portion. After 5 min the mixture was allowed to warm to room temperature. Water (0.2 mL) was added, and the mixture was evaporated under vacuum. Column chromatography (loaded as a slurry in dichloromethane, silica gel, step-wise gradient of 10% to 38% ethyl acetate in hexane) provided 4-(N-cyclohexylcarbonyl-N-(2-methyl-3-phenyl-2-(E)-propenyl)aminomethyl)-1-t-butoxycarbonylpiperidine (1.67 g, 88% yield) as a colorless gum. TLC R$_f$=0.19, 25% ethyl acetate in hexane.

To a solution of 4-(N-cyclohexylcarbonyl-N-(2-methyl-3-phenyl-2-(E)-propenyl)aminomethyl)-1-t-butoxycarbonylpiperidine (1.55 g, 3.4 mmol) in dichloromethane (15 mL) stirring at room temperature under argon, was added trifluoroacetic acid (3.7 g, 32 mmol). After 1 h toluene (15 mL) was added and the mixture was evaporated under vacuum. The residue was repeatedly dissolved in dichloromethane and evaporated under vacuum to obtain a colorless gum that solidified on standing. This gum contained 4-(N-cyclohexylcarbonyl-N-(2-methyl-3-phenyl-2-(E)-propenyl)aminomethyl)piperidine trifluoroacetic acid salt (1.59 g, quantitative yield) and trace residual trifluoroacetic acid.

To a solution of 4-(N-cyclohexylcarbonyl-N-(2-methyl-3-phenyl-2-(E)-propenyl)aminomethyl)piperidine trifluoroacetic acid salt (0.19 g, 0.41 mmol) and triethylamine (0.33 g, 3.3 mmol) in dichloromethane (6 mL) at room temperature, was added 3-phenylbenzenesulfonyl chloride (0.14 g, 0.53 mmol). The resulting mixture was stirred in a capped vial for 16 h before column chromatography (loaded after partial evaporation, silica gel, step-wise gradient of 15% to 40% ethyl acetate in hexane) provided the compound of Example 1 (0.23 g, 98% yield) as a colorless gum. The gum was solidified by trituration with methanol. A lyophilate was prepared by freeze-drying a solution of the compound of Example 1 in 1,4-dioxane. TLC R$_f$=0.52, 50% ethyl acetate in hexane. HPLC/MS [M+H]$^+$ 571.

Examples 2 to 27

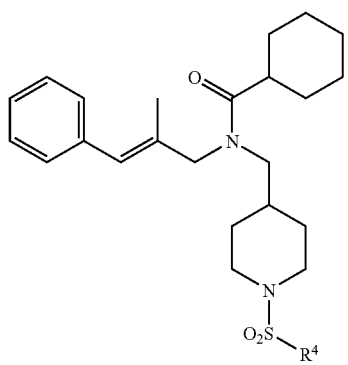

The compounds of Examples 2 to 27 (described below in Table 1) were prepared by sulfonylation reactions analogous to that used in the last step of the preparation of the compound of Example 1. The same amine intermediate (4-(N-cyclohexylcarbonyl-N-(2-methyl-3-phenyl-2-(E)-propenyl)aminomethyl)piperidine trifluoroacetic acid salt, 0.016-0.4 mmol) was coupled with the requisite sulfonyl chlorides. Typically, isolated yields ranged upward of 65%. In some cases, the desired product was isolated by reverse phase preparative HPLC rather than by column chromatography. In these cases, after the reaction mixture was evaporated under vacuum, the residue was stirred in N,N-dimethylformamide (20% of final volume), before methanol (75% of final volume) and water (5% of final volume) were added. If all solid dissolved, the resulting solution was injected to reverse phase preparative HPLC. If all solid did not dissolve, the supernatant was injected to reverse phase preparative HPLC, and the remaining solid was repeatedly subjected to the process of attempted dissolving in N,N-dimethylformamide, methanol, and water, followed by supernatant injection, until either all solid dissolved and was injected, or the solid was judged by HPLC/MS to either lack desired product or to be pure desired product. Any pure solid desired product was combined with pure desired product obtained from reverse phase preparative HPLC.

TABLE 1

| Example | R$^4$ | HPLC/MS observed [M + H]$^+$ |
|---|---|---|
| 2 | octyl | 531 |
| 3 | benzyl | 509 |
| 4 | (1R)-10-camphoryl | 569 |
| 5 | phenyl | 495 |
| 6 | 2-fluorophenyl | 513 |
| 7 | 2-chlorophenyl | 529, 531 |
| 8 | 2-bromophenyl | 573, 575 |
| 9 | 2-methylphenyl | 509 |
| 10 | 3-fluorophenyl | 513 |
| 11 | 3-chlorophenyl | 529, 531 |
| 12 | 3-bromophenyl | 573, 575 |
| 13 | 3-trifluoromethoxyphenyl | 579 |
| 14 | 3-methoxyphenyl | 525 |
| 15 | 3-methylphenyl | 509 |
| 16 | 3-phenoxyphenyl | 587 |
| 17 | 3-nitrophenyl | 540 |
| 18 | 2,3-dichlorophenyl | 563, 565, 567 |
| 19 | 2-methyl-3-chlorophenyl | 543, 545 |
| 20 | 2,6-difluorophenyl | 531 |
| 21 | 4-methylphenyl | 509 |
| 22 | 2-naphthyl | 545 |
| 23 | 5-chloronaphth-1-yl | 579, 581 |
| 24 | 8-quinolinyl | 546 |
| 25 | 6-isoquinolinyl | 546 |
| 26 | 4,5-dichlorothiophen-2-yl | 569, 571, 573 |
| 27 | dimethylamino | 462 |

Example 28

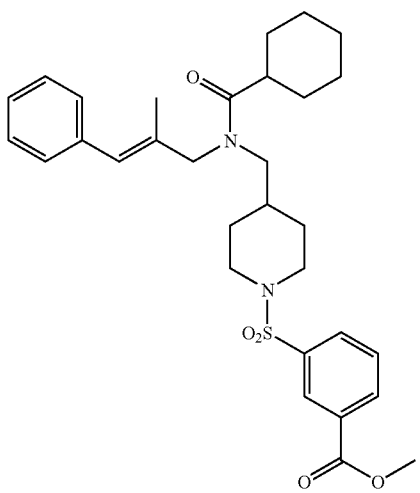

Example 28 was prepared from (4-(N-cyclohexylcarbonyl-N-(2-methyl-3-phenyl-2-(E)-propenyl)aminomethyl)piperidine trifluoroacetic acid salt analogously to the compound of Example 1, except that the sulfonyl chloride used was 3-carboxybenzenesulfonyl chloride and product isolation was by reverse phase preparative HPLC. In this case, the expected carboxylic acid product was partially methyl esterified upon exposure to methanol during the course of reverse phase preparative HPLC purification. Thus, the methyl ester, the compound of Example 28 (contaminated with the free acid), was obtained. HPLC/MS [M+H]$^+$ 553.

Examples 29 to 33

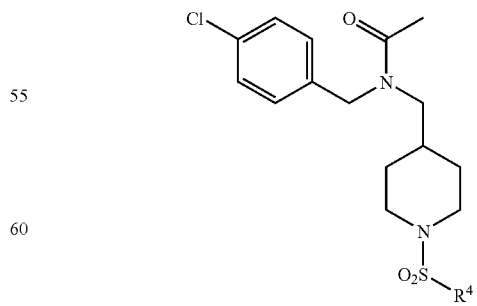

To a mixture of 1-t-butoxycarbonyl-4-carboxypiperidine (2.3 g, 10 mmol), 4-chlorobenzylamine (1.56 g, 11 mmol), and 1-hydroxy-7-azabenzotriazole (1.5 g, 11 mmol) in tetrahydrofuran (20 mL) at room temperature under argon, was added 1-[3-(dimethylamino)propyl]-3-ethylcarbodiimide hydrochloride (2.1 g, 11 mmol), and the resulting mixture was stirred for 16 h. The solvent was evaporated under vacuum, and the residue was dissolved in ethyl acetate (50 mL). The resulting solution was washed sequentially with 0.01 M aqueous hydrochloric acid (50 mL), 1.0 M aqueous sodium hydroxide (25 mL), and brine (25 mL) before drying (anhydrous sodium sulfate) and evaporation under vacuum to obtain 4-(N-(4-chlorobenzyl)aminocarbonyl)-1-t-butoxycarbonylpiperidine (3.6 g, quantitative yield).

To a solution of 4-(N-(4-chlorobenzyl)aminocarbonyl)-1-t-butoxycarbonylpiperidine (1.76 g, 5.0 mmol) in dry tetrahydrofuran (20 mL) stirring under argon at room temperature, was added borane-tetrahydrofuran complex (1.0 M in tetrahydrofuran, 20 mL, 20 mmol). The resulting solution was heated to 80° C. for 16 h before cooling to 0° C. Saturated aqueous ammonium chloride (20 mL) was added, and the resulting mixture was stirred for 30 min before extraction with ethyl acetate (25 mL three times). The combined extracts were dried (anhydrous sodium sulfate) and evaporated under vacuum to obtain a gum, which was purified by column chromatography (silica gel, 100% ethyl acetate) to provide 4-(N-(4-chlorobenzyl)aminomethyl)-1-t-butoxycarbonylpiperidine (1.37 g, 81% yield) as a white solid.

To a solution of 4-(N-(4-chlorobenzyl)aminomethyl)-1-t-butoxycarbonylpiperidine (300 mg, 0.89 mmol) and triethylamine (180 mg, 1.78 mmol) in tetrahydrofuran (15 mL) stirring at room temperature under argon, was added acetic anhydride (109 mg, 1.07 mmol) in a single portion. After 16 h the mixture was evaporated under vacuum. Column chromatography (silica gel, 65% ethyl acetate in hexane) provided 4-(N-acetyl-N-(4-chlorobenzyl)aminomethyl)-1-t-butoxycarbonylpiperidine (309 mg, 91% yield). TLC $R_f$=0.30, 65% ethyl acetate in hexane.

To a solution of 4-(N-acetyl-N-(4-chlorobenzyl)aminomethyl)-1-t-butoxycarbonylpiperidine (280 mg, 0.73 mmol) in dichloromethane (20 mL) stirring at room temperature, was added trifluoroacetic acid (5 mL). After 16 h the solvent was evaporated under vacuum, then toluene was added and evaporated (5 mL twice), followed by diethyl ether (10 mL twice) to obtain 4-(N-acetyl-N-(4-chlorobenzyl)aminomethyl)piperidine trifluoroacetic acid salt (298 mg, quantitative yield) as a tan solid.

The compounds of Examples 29 to 33 (described below in Table 2) were prepared by sulfonylation reactions analogous to those used in the preparation of the compound of Example 1 and the compounds of Examples 2 to 27, but coupling 4-(N-acetyl-N-(4-chlorobenzyl)aminomethyl)piperidine trifluoroacetic acid salt with the requisite sulfonyl chlorides.

TABLE 2

| Example | R⁴ | HPLC/MS observed [M + Na]⁺ |
| --- | --- | --- |
| 29 | 3-chlorophenyl | 477, 479, 481 |
| 30 | 3-trifluoromethoxyphenyl | 527, 529 |
| 31 | 3-methoxyphenyl | 473, 475 |
| 32 | 3-methylphenyl | 457, 459 |
| 33 | 3-phenylphenyl | 519, 521 |

Example 34

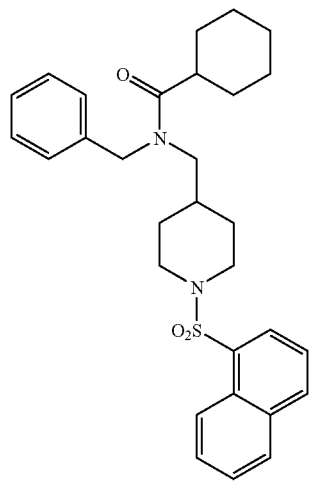

To a suspension of 4-aminocarbonylpiperidine (12.8 g, 100 mmol) in dry tetrahydrofuran (250 μL) containing triethylamine (20.2 g, 200 mmol) stirring at room temperature under argon, was added 1-naphthalenesulfonyl chloride (25 g, 110 mmol). After 16 h the solvent was evaporated under vacuum, and a solution of 25% methanol in diethyl ether (250 mL) was added to the residue. The resulting mixture was stirred for 2 h before the solid was filtered. The solid was washed with diethyl ether (50 mL twice), then water (50 mL twice), followed by diethyl ether (50 mL twice) again before drying under vacuum. This provided 4-aminocarbonyl-1-(1-naphthylsulfonyl)piperidine (27.9 g, 88% yield) as a white solid.

To a solution of 4-aminocarbonyl-1-(1-naphthylsulfonyl)piperidine (10.6 g, 33.3 mmol) in tetrahydrofuran (200 mL) stirring under argon at room temperature, was added borane-tetrahydrofuran complex (1.5 M in tetrahydrofuran, 67 mL, 100 mmol). The resulting solution was heated to 80° C. for 6 h before the solvent was evaporated under vacuum. The residue was dissolved in 1.0 M aqueous hydrochloric acid (100 mL), and this was washed with diethyl ether (100 mL twice). The aqueous layer was basified to pH 10 with 50% aqueous sodium hydroxide and extracted with dichloromethane (50 mL three times). The combined dichloromethane extracts were dried (anhydrous sodium sulfate) and evaporated under vacuum to obtain 4-aminomethyl-1-(1-naphthylsulfonyl)piperidine (9.1 g, 90% yield).

To a solution of 4-aminomethyl-1-(1-naphthylsulfonyl)piperidine (608 mg, 2.0 mmol) and triethylamine (303 mg, 3.0 mmol) in dichloromethane (30 mL) stirring at room temperature under argon, was added cyclohexanecarbonyl chloride (325 mg, 2.2 mmol) in a single portion. After 2 h the solvent was evaporated under vacuum, and the residue was slurried with diethyl ether and filtered. The filtrate was evaporated, and purification by column chromatography (silica gel, ethyl acetate in hexane) provided 4-(N-cyclohexylcarbonylaminomethyl)-1-(1-naphthylsulfonyl)piperidine (793 mg, 96% yield) as a gum.

To a solution of 4-(N-cyclohexylcarbonylaminomethyl)-1-(1-naphthylsulfonyl)piperidine (83 mg, 0.20 mmol) in dry tetrahydrofuran (5 mL) stirring at 0° C. under argon, was added sodium methoxide (13 mg, 0.24 mmol) followed by benzyl bromide (103 mg, 0.60 mmol). The reaction mixture was heated to 80° C. for 6 h before the solvent was evaporated under vacuum. Reverse phase preparative HPLC allowed isolation of the compound of Example 34 (11 mg, 11% yield) as a white solid. HPLC/MS [M+H]+ 505.

Example 35

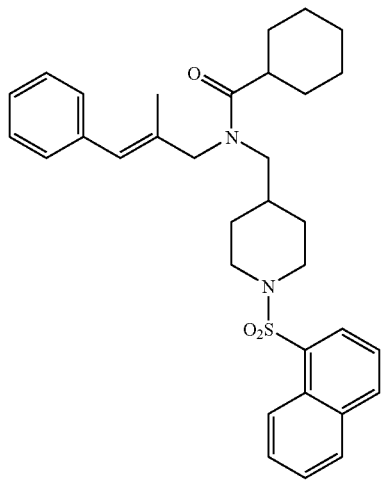

A mixture of 4-aminomethyl-1-(1-naphthylsulfonyl)piperidine (intermediate in the preparation of the compound of Example 34, 450 mg, 1.5 mmol), (E)-2-methyl-3-phenylpropenal (438 mg, 3.0 mmol), acetic acid (240 mg, 4.0 mmol), and 1,2-dichloroethane (50 mL) was stirred under argon at room temperature for 3 h before sodium triacetoxyborohydride (1.27 g, 6.0 mmol) and more acetic acid (360 mg, 6.0 mmol) were added. After 16 h saturated aqueous sodium bicarbonate (50 mL) was added, and the aqueous and organic phases were separated. The aqueous phase was extracted with dichloromethane (50 mL twice), and the combined organic phases were dried (anhydrous sodium sulfate) and evaporated under vacuum. Column chromatography (silica gel, gradient of ethyl acetate in hexane rising to 100% ethyl acetate) provided 4-(N-(2-methyl-3-phenyl-2-(E)-propenyl)aminomethyl)-1-(1-naphthylsulfonyl)piperidine (561 mg, 86% yield) as an oil. TLC $R_f$=0.18, 100% ethyl acetate.

To a solution of 4-(N-(2-methyl-3-phenyl-2-(E)-propenyl) aminomethyl)-1-(1-naphthylsulfonyl)piperidine (123 mg, 0.28 mmol) and triethylamine (57 mg, 0.57 mmol) in dichloromethane (20 mL) stirring at room temperature under argon, was added cyclohexanecarbonyl chloride (50 mg, 0.34 mmol) in a single portion. After 30 min the solvent was evaporated under vacuum. Column chromatography (silica gel, gradient of 0% to 50% ethyl acetate in hexane) provided the compound of Example 35 (137 mg, 90% yield) as a white solid. A lyophilate was prepared by freeze-drying a solution of the compound of Example 35 in a mixture of 1,4-dioxane and water. HPLC/MS [M+H]+ 545.

Examples 36 to 47

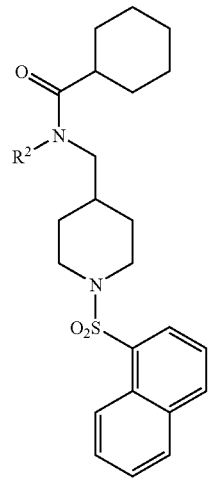

The compounds of Examples 36 to 47 (described below in Table 3) were prepared in two steps from 4-aminomethyl-1-(1-naphthylsulfonyl)piperidine by reductive amination followed by acylation in a manner analogous to the preparation of the compound of Example 35. In these cases, the reductive amination reactions employed the requisite aldehydes (3-chlorobenzaldehyde, etc.) in smaller excess over amine to produce optimal desired product yields. Dichloromethane was sometimes used as the reaction solvent instead of 1,2-dichloroethane. Reductive amination product purification could be performed by column chromatography eluting with concentrated aqueous ammonium hydroxide—methanol—dichloromethane mixtures or ethyl acetate—hexane mixtures, or by reverse phase preparative HPLC with trifluoroacetic acid containing solvents. Reductive amination products were acylated with cyclohexanecarbonyl chloride as in the case of the compound of Example 35. For the final step, reverse phase preparative HPLC was used in some cases instead of column chromatography.

TABLE 3

| Example | $R^2$ | HPLC/MS observed [M + H]+ except Ex. 38 |
|---|---|---|
| 36 | 3-chlorobenzyl | 539, 541 |
| 37 | 4-chlorobenzyl | 539, 541 |
| 38 | 4-methoxybenzyl | [M + Na]+ 557 |
| 39 | 2-naphthylmethyl | 555 |
| 40 | $H_2C=C(CH_3)CH_2$— | 469 |
| 41 | (E) $H_3CCH=C(CH_3)CH_2$— | 483 |
| 42 | 1-cyclohexenylmethyl | 509 |
| 43 | (E) $H_3CCH_2O_2CCH=C(CH_3)CH_2$— | 541 |
| 44 | (R,S) $H_3CCH_2O_2CCH(CH_3)CH_2$— | 529 |
| 45 | 2-pyridylmethyl | 506 |
| 46 | 3-pyridylmethyl | 506 |
| 47 | 4-pyridylmethyl | 506 |

Example 48

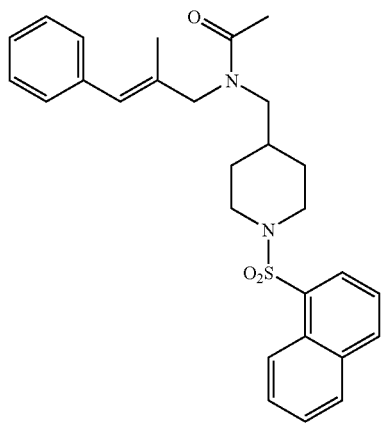

To a solution of 4-(N-(2-methyl-3-phenyl-2-(E)-propenyl) aminomethyl)-1-(1-naphthylsulfonyl)piperidine (intermediate in the preparation of the compound of Example 35, 500 mg, 1.15 mmol) and triethylamine (233 mg, 2.3 mmol) in dichloromethane (20 mL) stirring at room temperature under argon, was added acetic anhydride (235 mg, 2.3 mmol) in a single portion. After 20 min the solvent was evaporated under vacuum. Column chromatography (silica gel, ethyl acetate in hexane) provided the compound of Example 48 (486 mg, 89% yield) as a white solid. HPLC/MS [M+H]$^+$ 477.

Examples 49 to 57

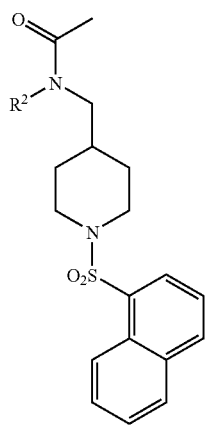

The compounds of Examples 49 to 57 (described below in Table 4) were prepared from the reductive amination products that were prepared as intermediates in synthesis of the compounds of Examples 36 to 47. These reductive amination product were acetylated by the procedure used in the preparation of the compound of Example 48, except that only 1.2 equiv acetic anhydride was used. Reverse phase preparative HPLC was used in some cases instead of column chromatography.

TABLE 4

| Example | R$^2$ | HPLC/MS observed [M + H]$^+$ or [M + Na]$^+$ |
|---|---|---|
| 49 | 3-chlorobenzyl | [M + H]$^+$ 471, 473 |
| 50 | 4-chlorobenzyl | [M + Na]$^+$ 493, 495 |
| 51 | 4-methoxybenzyl | [M + Na]$^+$ 489 |
| 52 | 2-naphthylmethyl | [M + Na]$^+$ 509 |
| 53 | H$_2$C=C(CH$_3$)CH$_2$— | [M + H]$^+$ 401 |
| 54 | (E) H$_3$CCH=C(CH$_3$)CH$_2$— | [M + H]$^+$ 415 |
| 55 | 1-cyclohexenylmethyl | [M + H]$^+$ 441 |
| 56 | (E) CH$_3$CH$_2$O$_2$CCH=C(CH$_3$)CH$_2$— | [M + Na]$^+$ 495 |
| 57 | (R,S) CH$_3$CH$_2$O$_2$CCH(CH$_3$)CH$_2$— | [M + Na]$^+$ 483 |

Example 58

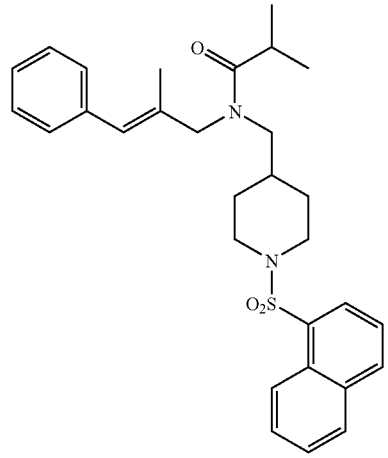

To a solution of 4-(N-(2-methyl-3-phenyl-2-(E)-propenyl) aminomethyl)-1-(1-naphthylsulfonyl)piperidine (intermediate in the preparation of the compound of Example 35, 22 mg, 0.05 mmol) and triethylamine (10 mg, 0.10 mmol) in dichloromethane (5 mL) stirring at room temperature under argon, was added isobutyryl chloride (6.4 mg, 0.06 mmol) in a single portion. After 30 min the solvent was evaporated under vacuum. Reverse phase preparative HPLC (trifluoroacetic acid containing solvents were used) provided the compound of Example 58 (13 mg, 50% yield) as a white solid. HPLC/MS [M+H]$^+$ 505.

Examples 59 to 62

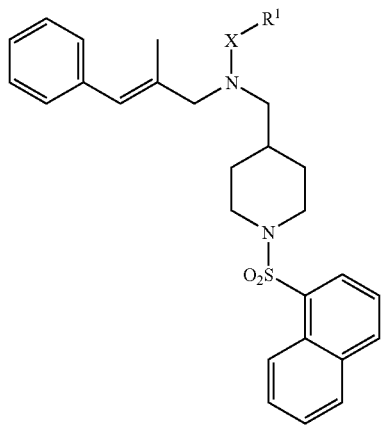

The compounds of Examples 59 to 62 (described below in Table 5) were prepared from 4-(N-(2-methyl-3-phenyl-2-(E)-propenyl)aminomethyl)-1-(1-naphthylsulfonyl)piperidine analogously to the compound of Example 58, except that instead of isobutyryl chloride, other electrophiles were required (methanesulfonyl chloride, methyl chloroformate, morpholin-4-ylcarbonyl chloride, and pyridyl-2-carbonyl chloride).

TABLE 5

| Example | $R^1$-X | HPLC/MS observed $[M + H]^+$ |
|---|---|---|
| 59 | methylsulfonyl | 513 |
| 60 | methoxycarbonyl | 493 |
| 61 | morpholin-4-yl-carbonyl | 548 |
| 62 | TFA•pyridin-2-yl-carbonyl | 540 |

Example 63

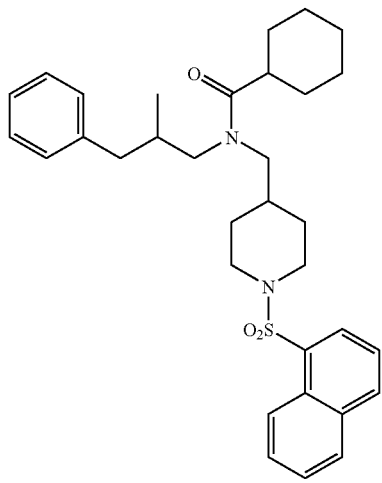

To a solution of the compound of Example 35 (15 mg, 0.027 mmol) in methanol (5 mL) stirring at room temperature, was added 10% palladium on carbon (3 mg). The resulting mixture was hydrogenated on a Parr shaker at 50 psi for 16 h. The catalyst was filtered, rinsing with methanol and ethyl acetate, and the filtrate was evaporated under vacuum. Reverse phase preparative HPLC provided the compound of Example 63 (9.6 mg, 65% yield) as a solid. HPLC/MS $[M+H]^+$ 547.

Biological Evaluation

Cannabinoid Receptor Binding Assay

Radioligand binding studies were conducted in membranes prepared from Chinese Hamster Ovary (CHO) cells that over-express recombinant human CB-1 (CHO-CB-1 cells). Total assay volume for the binding studies was 100 μl. 5 μg of membranes were brought up to a final volume of 95 μl with Binding Buffer (25 mM HEPES, 150 mM NaCl, 2.5 mM $CaCl_2$, 1 mM $MgCl_2$, 0.25% BSA). The diluted membranes were preincubated with a compound or DMSO vehicle. The binding reaction was initiated by the addition of 2 nM final $^3$H-CP-55,940 (120 Ci/mmol) and proceeded for 2.5 hours at room temperature. The binding reaction was terminated by transferring the reaction to GF/B 96 well plates (presoaked with 0.3% polyethylenimine) using a Packard Cell Harvester. The filter was washed with 0.25×PBS, 30 μl MicroScint was added per well, and the bound radiolabel was quantitated by scintillation counting on a Packard TopCount Scintillation Counter. The CB-2 radioligand binding assay was conducted identically except that the membranes from CHO-CB-2 cells were used.

For a compound to be considered a CB-1 antagonist, the compound must possess a CB-1 receptor binding affinity Ki less than 13000 nM. As determined by the assay described above, the CB-1 receptor binding $K_i$ values of working Examples 1-63 fall within the range of 0.01 nM to 10000 nM.

Cannabinoid Receptor Functional Activity Assay

Functional CB-1 inverse agonist activity of test compounds was determined in CHO-CB-1 cells using a cAMP accumulation assay. CHO-CB-1 cells were grown in 96 well plates to near confluence. On the day of the functional assay, growth medium was aspirated and 100 of Assay Buffer (PBS plus 25 mM HEPES/0.1 mM 3-isobutyl-1-methylxanthine/ 0.1% BSA) was added. Compounds were added to the Assay buffer diluted 1:100 from 100% DMSO and allowed to pre-incubate for 10 minutes prior to addition of 5 uM forskolin. The mixture was allowed to proceed for 15 minutes at room temperature and was terminated by the addition of 0.1 N HCl. The total intracellular cAMP concentration was quantitated using the Amersham cAMP SPA kit.

Utilities and Combinations

Utilities

The compounds of the present invention are cannabinoid receptor modulators, and include compounds which are, for example, selective agonists, partial agonists, inverse agonists, antagonists or partial antagonists of the cannabinoid receptor. Accordingly, the compounds of the present invention may be useful for the treatment or prevention of diseases and disorders associated with G-protein coupled cannabinoid receptor activity. Preferably, compounds of the present invention possess activity as antagonists or inverse agonists of the CB-1 receptor, and may be used in the treatment of diseases or disorders associated with the activity of the CB-1 receptor.

Accordingly, the compounds of the present invention can be administered to mammals, preferably humans, for the treatment of a variety of conditions and disorders, including, but not limited to metabolic and eating disorders as well as conditions associated with metabolic disorders, (e.g., obesity, diabetes, arteriosclerosis, hypertension, polycystic ovary disease, cardiovascular disease, osteoarthritis, dermatological disorders, hypertension, insulin resistance, hypercholesterolemia, hypertriglyceridemia, cholelithiasis and sleep disorders, hyperlipidemic conditions, bulimia nervosa and compulsive eating disorders) or psychiatric disorders, such as substance abuse, depression, anxiety, mania and schizophrenia. These compounds could also be used for the improvement of cognitive function (e.g., the treatment of dementia, including Alzheimer's disease, short term memory loss and attention deficit disorders); neurodegenerative disorders (e.g., Parkinson's Disease, cerebral apoplexy and craniocerebral trauma) and hypotension (e.g., hemorrhagic and endotoxin-induced hypotension). These compounds could also be used for treatment of catabolism in connection with pulmonary dysfunction and ventilator dependency; treatment of cardiac dysfunction (e.g., associated with valvular disease, myocardial infarction, cardiac hypertrophy or congestive heart failure); and improvement of the overall pulmonary function; transplant rejection; rheumatoid arthritis; multiple sclerosis; inflammatory bowel disease; lupus; graft vs. host disease; T-cell mediated hypersensitivity disease; psoriasis; asthma; Hashimoto's thyroiditis; Guillain-Barre syndrome; cancer; contact dermatitis; allergic rhinitis; and ischemic or reperfusion injury.

Compounds useful in the treatment of appetitive or motivational disorders regulate desires to consume sugars, carbohydrates, alcohol or drugs and more generally to regulate the consumption of ingredients with hedonic value. In the present description and in the claims, appetitive disorders are understood as meaning: disorders associated with a substance and especially abuse of a substance and/or dependency on a substance, disorders of eating behaviors, especially those liable to cause excess weight, irrespective of its origin, for example: bulimia nervosa, craving for sugars. The present invention therefore further relates to the use of a CB-1 receptor antagonist or inverse agonist for the treatment of bulimia and obesity, including obesity associated with type II diabetes (non-insulin-dependent diabetes), or more generally any disease resulting in the patient becoming overweight. Obesity, as described herein, is defined by a body mass index (kg/m$^2$) of at least 26. It may be due to any cause, whether genetic or environmental, including overeating and bulemia, polycycstic ovary disease, craniopharyngeoma, Prader-Willi Syndrome, Frohlich's Syndrome, Type II diabetes, growth hormone deficiency, Turner's Syndrome and other pathological states characterized by reduced metabolic activity or reduced energy expenditure. As used with reference to the utilities described herein, the term "treating" or "treatment" encompasses prevention, partial alleviation, or cure of the disease or disorder. Further, treatment of obesity is expected to prevent progression of medical covariants of obesity, such as arteriosclerosis, Type II diabetes, polycystic ovary disease, cardiovascular disease, osteoarthritis, dermatological disorders, hypertension, insulin resistance, hypercholesterolemia, hypertriglyceridemia, cholelithiasis and sleep disorders.

Compounds in the present invention may also be useful in treating substance abuse disorders, including substance dependence or abuse without physiological dependence. Substances of abuse include alcohol, amphetamines (or amphetamine-like substances), caffeine, cannabis, cocaine, hallucinogens, inhalents, nicotine, opioids, phencyclidine (or phencyclidine-like compounds), sedative-hypnotics or benzodiazepines, and other (or unknown) substances and combinations of the above. The terms "substance abuse disorders" also includes drug or alcohol withdrawal syndromes and substance-induced anxiety or mood disorder with onset during withdrawal.

Compounds in the present invention may be useful in treating memory impairment and cognitive disorders. The condition of memory impairment is manifested by impairment of the ability to learn new information and/or the inability to recall previously learned information. Memory impairment is a primary symptom of dementia and can also be a symptom associated with such diseases as Alzheimer's disease, schizophrenia, Parkinson's disease, Huntington's disease, Pick's disease, Creutzfeld-Jakob disease, HIV, cardiovascular disease, and head trauma as well as age-related cognitive decline. Dementias are diseases that include memory loss and additional intellectual impairment separate from memory. Cannabinoid receptor modulators may also be useful in treating cognitive impairments related to attentional deficits, such as attention deficit disorder.

Compounds in the present invention may also be useful in treating diseases associated with dysfunction of brain dopaminergic systems, such as Parkinson's Disease and substance abuse disorders. Parkinsons's Disease is a neurodenerative movement disorder characterized by bradykinesia and tremor.

As modulators of the cannabinoid receptor, the compounds of the present invention are further useful for the treatment and prevention of respiratory diseases and disorders. Respiratory diseases for which cannabinoid receptor modulators are useful include, but are not limited to, chronic pulmonary obstructive disorder, emphysema, asthma, and bronchitis. In addition, cannabinoid receptor modulators block the activation of lung epithelial cells by moeties such as allergic agents, inflammatory cytokines or smoke, thereby limiting release of mucin, cytokines, and chemokines, or selectively inhibiting lung epithelial cell activation.

Moreover, the compounds employed in the present invention may stimulate inhibitory pathways in cells, particularly in leukocytes, lung epithelial cells, or both, and are thus useful in treating such diseases. "Leukocyte activation" is defined herein as any or all of cell proliferation, cytokine production, adhesion protein expression, and production of inflammatory mediators. "Epithelial cell activation" is defined herein as the production of any or all of mucins, cytokines, chemokines, and adhesion protein expression.

Use of the compounds of the present invention for treating leukocyte activation-associated disorders is exemplified by, but is not limited to, treating a range of disorders such as: transplant (such as organ transplant, acute transplant, xenotransplant or heterograft or homograft (such as is employed in burn treatment)) rejection; protection from ischemic or reperfusion injury such as ischemic or reperfusion injury incurred during organ transplantation, myocardial infarction, stroke or other causes; transplantation tolerance induction; arthritis (such as rheumatoid arthritis, psoriatic arthritis or osteoarthritis); multiple sclerosis; respiratory and pulmonary diseases including but not limited to chronic obstructive pulmonary disease (COPD), emphysema, bronchitis, and acute respiratory distress syndrome (ARDS); inflammatory bowel disease, including ulcerative colitis and Crohn's disease; lupus (systemic lupus erythematosis); graft vs. host disease; T-cell mediated hypersensitivity diseases, including contact hypersensitivity, delayed-type hypersensitivity, and gluten-sensitive enteropathy (Celiac disease); psoriasis; contact dermatitis (including that due to poison ivy); Hashimoto's thyroiditis; Sjogren's syndrome; Autoimmune Hyperthyroidism, such as Graves' Disease; Addison's disease (autoimmune disease of the adrenal glands); Autoimmune polyglandular disease (also known as autoimmune polyglandular syndrome); autoimmune alopecia; pernicious anemia; vitiligo; autoimmune hypopituatarism; Guillain-Barre syndrome; other autoimmune diseases; glomerulonephritis; serum sickness; uticaria; allergic diseases such as respiratory allergies (asthma, hayfever, allergic rhinitis) or skin allergies; scleracierma; mycosis fungoides; acute inflammatory and respiratory responses (such as acute respiratory distress syndrome and ishchemia/reperfusion injury); dermatomyositis; alopecia greata; chronic actinic dermatitis; eczema; Behcet's disease; Pustulosis palmoplanteris; Pyoderma gangrenum; Sezary's syndrome; atopic dermatitis; systemic schlerosis; and morphea. The term "leukocyte activation-associated" or "leukocyte-activation mediated" disease as used herein includes each of the above referenced diseases or disorders. In a particular embodiment, the compounds of the present invention are useful for treating the aforementioned exemplary disorders irrespective of their etiology. The combined activity of the present compounds towards monocytes, macrophages, T-cells, etc. may be useful in treating any of the above-mentioned disorders.

Cannabinoid receptors are important in the regulation of Fc gamma receptor responses of monocytes and macrophages. Compounds of the present invention inhibit the Fc gamma dependent production of TNF alpha in human monocytes/macrophages. The ability to inhibit Fc gamma receptor dependent monocyte and macrophage responses results in additional anti-inflammatory activity for the present compounds. This activity is especially of value, for example, in treating inflammatory diseases such as arthritis or inflammatory bowel disease. In particular, the present compounds are useful for treating autoimmune glomerulonephritis and other instances of glomerulonephritis induced by deposition of immune complexes in the kidney that trigger Fc gamma receptor responses leading to kidney damage.

Cannabinoid receptors are expressed on lung epithelial cells. These cells are responsible for the secretion of mucins and inflammatory cytokines/chemokines in the lung and are thus intricately involved in the generation and progression of respiratory diseases. Cannabinoid receptor modulators regulate both the spontaneous and the stimulated production of both mucins and cytokines. Thus, such compounds are useful in treating respiratory and pulmonary diseases including, COPD, ARDS, and bronchitis.

Further, cannabinoid receptors may be expressed on gut epithelial cells and hence regulate cytokine and mucin production and may be of clinical use in treating inflammatory diseases related to the gut. Cannabinoid receptors are also expressed on lymphocytes, a subset of leukocytes. Thus, cannabinoid receptor modulators will inhibit B and T-cell activation, proliferation and differentiation. Thus, such compounds will be useful in treating autoimmune diseases that involve either antibody or cell mediated responses such as multiple sclerosis and lupus.

In addition, cannabinoid receptors regulate the Fc epsilon receptor and chemokine induced degranulation of mast cells and basophils. These play important roles in asthma, allergic rhinitis, and other allergic disease. Fc epsilon receptors are stimulated by IgE-antigen complexes. Compounds of the present invention inhibit the Fc epsilon induced degranulation responses, including the basophil cell line, RBL. The ability to inhibit Fc epsilon receptor dependent mast cell and basophil responses results in additional anti-inflammatory and anti-allergic activity for the present compounds. In particular, the present compounds are useful for treating asthma, allergic rhinitis, and other instances of allergic disease.

Combinations

The present invention includes within its scope pharmaceutical compositions comprising, as an active ingredient, a therapeutically effective amount of at least one of the compounds of formula I, alone or in combination with a pharmaceutical carrier or diluent. Optionally, compounds of the present invention can be used alone, in combination with other suitable therapeutic agents useful in the treatment of the aforementioned disorders including: anti-obesity agents; anti-diabetic agents, appetite suppressants; cholesterol/lipid-lowering agents, HDL-raising agents, cognition enhancing agents, agents used to treat neurodegeneration, agents used to treat respiratory conditions, agents used to treat bowel disorders, anti-inflammatory agents; anti-anxiety agents; anti-depressants; anti-hypertensive agents; cardiac glycosides; and anti-tumor agents.

Such other therapeutic agent(s) may be administered prior to, simultaneously with, or following the administration of the cannabinoid receptor modulators in accordance with the invention.

Examples of suitable anti-obesity agents for use in combination with the compounds of the present invention include melanocortin receptor (MC4R) agonists, melanin-concentrating hormone receptor (MCHR) antagonists, growth hormone secretagogue receptor (GHSR) antagonists, galanin receptor modulators, orexin antagonists, CCK agonists, GLP-1 agonists, and other Pre-proglucagon-derived peptides; NPY1 or NPY5 antagonsist, NPY2 and NPY4 modulators, corticotropin releasing factor agonists, histamine receptor-3 (H3) modulators, aP2 inhibitors, PPAR gamma modulators, PPAR delta modulators, acetyl-CoA carboxylase (ACC) inhibitors, 11-β-HSD-1 inhibitors, adinopectin receptor modulators; beta 3 adrenergic agonists, such as AJ9677 (Takeda/Dainippon), L750355 (Merck), or CP331648 (Pfizer) or other known beta 3 agonists as disclosed in U.S. Pat. Nos. 5,541,204, 5,770,615, 5,491,134, 5,776,983 and 5,488,064, a thyroid receptor beta modulator, such as a thyroid receptor ligand as disclosed in WO 97/21993 (U. Cal SF), WO 99/00353 (KaroBio) and GB98/284425 (KaroBio), a lipase inhibitor, such as orlistat or ATL-962 (Alizyme), serotonin receptor agonists, (e.g., BVT-933 (Biovitrum)), monoamine reuptake inhibitors or releasing agents, such as fenfluramine, dexfenfluramine, fluvoxamine, fluoxetine, paroxetine, sertraline, chlorphentermine, cloforex, clortermine, picilorex, sibutramine, dexamphetamine, phentermine, phenylpropanolamine or mazindol, anorectic agents such as topiramate (Johnson & Johnson), CNTF (ciliary neurotrophic factor)/Axokine® (Regeneron), BDNF (brain-derived neurotrophic factor), leptin and leptin receptor modulators, or cannabinoid-1 receptor antagonists, such as SR-141716 (Sanofi) or SLV-319 (Solvay).

Examples of suitable anti-diabetic agents for use in combination with the compounds of the present invention include: insulin secretagogues or insulin sensitizers, which may include biguanides, sulfonyl ureas, glucosidase inhibitors, aldose reductase inhibitors, PPAR γ agonists such as thiazolidinediones, PPAR α agonists (such as fibric acid derivatives), PPAR δ antagonists or agonists, PPAR α/γ dual agonists, 11-β-HSD-1 inhibitors, dipeptidyl peptidase IV (DP4) inhibitors, SGLT2 inhibitors, glycogen phosphorylase inhibitors, and/or meglitinides, as well as insulin, and/or glucagon-like peptide-1 (GLP-1), GLP-1 agonist, and/or a PTP-1B inhibitor (protein tyrosine phosphatase-1B inhibitor).

The antidiabetic agent may be an oral antihyperglycemic agent preferably a biguanide such as metformin or phenformin or salts thereof, preferably metformin HCl. Where the antidiabetic agent is a biguanide, the compounds of the present invention will be employed in a weight ratio to biguanide within the range from about 0.001:1 to about 10:1, preferably from about 0.01:1 to about 5:1.

The antidiabetic agent may also preferably be a sulfonyl urea such as glyburide (also known as glibenclamide), glimepiride (disclosed in U.S. Pat. No. 4,379,785), glipizide, gliclazide or chlorpropamide, other known sulfonylureas or other antihyperglycemic agents which act on the ATP-dependent channel of the beta-cells, with glyburide and glipizide being preferred, which may be administered in the same or in separate oral dosage forms. The oral antidiabetic agent may also be a glucosidase inhibitor such as acarbose (disclosed in U.S. Pat. No. 4,904,769) or miglitol (disclosed in U.S. Pat. No. 4,639,436), which may be administered in the same or in a separate oral dosage forms.

The compounds of the present invention may be employed in combination with a PPAR γ agonist such as a thiazolidinedione oral anti-diabetic agent or other insulin sensitizers (which has an insulin sensitivity effect in NIDDM patients) such as rosiglitazone (SKB), pioglitazone (Takeda), Mitsubishi's MCC-555 (disclosed in U.S. Pat. No. 5,594,016), Glaxo-Welcome's GL-262570, englitazone (CP-68722, Pfizer) or darglitazone (CP-86325, Pfizer, isaglitazone (MIT/J&J), JTT-501 (JPNT/P&U), L-895645 (Merck), R-119702 (Sankyo/WL), NN-2344 (Dr. Reddy/NN), or YM-440 (Yamanouchi), preferably rosiglitazone and pioglitazone.

The compounds of the present invention may be employed with a PPARα/γ dual agonist such as MK-767/KRP-297 (Merck/Kyorin; as described in, K. Yajima, et. al., *Am. J. Physiol. Endocrinol. Metab.*, 284: E966-E971 (2003)), AZ-242 (tesaglitazar; Astra-Zeneca; as described in B. Ljung, et. al., *J. Lipid Res.*, 43, 1855-1863 (2002)); muraglitazar; or the compounds described in U.S. Pat. No. 6,414,002.

The compounds of the present invention may be employed in combination with anti-hyperlipidemia agents, or agents used to treat arteriosclerosis. An example of an hypolipidemic agent would be an HMG CoA reductase inhibitor which includes, but is not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin disclosed in U.S. Pat. Nos. 5,006,530 and 5,177,080, atorvastatin disclosed in U.S. Pat. Nos. 4,681,893, 5,273,995, 5,385,929 and 5,686,104, pitavastatin (Nissan/Sankyo's nisvastatin (NK-104) or itavastatin), disclosed in U.S. Pat. No. 5,011,930, Shionogi-Astra/Zeneca rosuvastatin (visastatin (ZD-4522)) disclosed in U.S. Pat. No. 5,260,440, and related statin compounds disclosed in U.S. Pat. No. 5,753,675, pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)-alkyl)pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propane-phosphonic acid derivatives as disclosed in French Patent No. 2,596,393, 2,3-disubstituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No. 0,142,146 A2, and quinoline and pyridine derivatives disclosed in U.S. Pat. Nos. 5,506,219 and 5,691,322. In addition, phosphinic acid compounds useful in inhibiting HMG CoA reductase suitable for use herein are disclosed in GB 2205837.

The squalene synthetase inhibitors suitable for use herein include, but are not limited to, α-phosphono-sulfonates disclosed in U.S. Pat. No. 5,712,396, those disclosed by Biller, et al., *J. Med. Chem.*, 31, 1869-1871 (1998) including isoprenoid (phosphinyl-methyl)phosphonates as well as other known squalene synthetase inhibitors, for example, as disclosed in U.S. Pat. Nos. 4,871,721 and 4,924,024 and in Biller, S. A., Neuenschwander, K., Ponpipom, M. M., and Poulter, C. D., *Current Pharmaceutical Design*, 2, 1-40 (1996).

In addition, other squalene synthetase inhibitors suitable for use herein include the terpenoid pyrophosphates disclosed by P. Ortiz de Montellano, et al., *J. Med. Chem.*, 20, 243-249 (1977), the farnesyl diphosphate analog A and presqualene pyrophosphate (PSQ-PP) analogs as disclosed by Corey and Volante, *J. Am. Chem. Soc.*, 98, 1291-1293 (1976), phosphinylphosphonates reported by McClard, R. W. et al., *J. Am. Chem. Soc.*, 109, 5544 (1987) and cyclopropanes reported by Capson, T. L., PhD dissertation, June, 1987, Dept. Med. Chem. U of Utah, Abstract, Table of Contents, pp 16, 17, 40-43, 48-51, Summary.

Other hypolipidemic agents suitable for use herein include, but are not limited to, fibric acid derivatives, such as fenofibrate, gemfibrozil, clofibrate, bezafibrate, ciprofibrate, clinofibrate and the like, probucol, and related compounds as disclosed in U.S. Pat. No. 3,674,836, probucol and gemfibrozil being preferred, bile acid sequestrants such as cholestyramine, colestipol and DEAE-Sephadex (SECHOLEX, POLICEXIDE) and cholestagel (Sankyo/Geltex), as well as lipostabil (Rhone-Poulenc), Eisai E-5050 (an N-substituted ethanolamine derivative), imanixil (HOE-402), tetrahydrolipstatin (THL), istigmastanylphos-phorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid (niacin), acipimox, acifran, neomycin, p-aminosalicylic acid, aspirin, poly(diallylmethylamine) derivatives such as disclosed in U.S. Pat. No. 4,759,923, quaternary amine poly (diallyldimethylammonium chloride) and ionenes such as disclosed in U.S. Pat. No. 4,027,009, and other known serum cholesterol lowering agents.

The other hypolipidemic agent may be an ACAT inhibitor (which also has anti-atherosclerosis activity) such as disclosed in, *Drugs of the Future*, 24, 9-15 (1999), (Avasimibe); "The ACAT inhibitor, C1-1011 is effective in the prevention and regression of aortic fatty streak area in hamsters", Nicolosi et al., *Atherosclerosis* (Shannon, Irel), 137 (1), 77-85 (1998); "The pharmacological profile of FCE 27677: a novel ACAT inhibitor with potent hypolipidemic activity mediated by selective suppression of the hepatic secretion of ApoB100-containing lipoprotein", Ghiselli, Giancarlo, *Cardiovasc. Drug Rev.*, 16 (1), 16-30 (1998); "RP 73163: a bioavailable alkylsulfinyl-diphenylimidazole ACAT inhibitor", Smith, C., et al., *Bioorg. Med. Chem. Lett*, 6 (1), 47-50 (1996); "ACAT inhibitors: physiologic mechanisms for hypolipidemic and anti-atherosclerotic activities in experimental animals", Krause et al., Editor(s): Ruffolo, Robert R., Jr.; Hollinger, Mannfred A., *Inflammation: Mediators Pathways*, 173-98 (1995), Publisher: CRC, Boca Raton, Fla.; "ACAT inhibitors:

potential anti-atherosclerotic agents", Sliskovic et al., *Curr. Med. Chem.*, 1 (3), 204-25 (1994); "Inhibitors of acyl-CoA: cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)-methyl]ureas with enhanced hypocholesterolemic activity", Stout et al., *Chemtracts: Org. Chem.,* 8 (6), 359-62 (1995), or TS-962 (Taisho Pharmaceutical Co. Ltd), as well as F-1394, CS-505, F-12511, HL-004, K-10085 and YIC-C8-434.

The hypolipidemic agent may be an upregulator of LDL receptor activity such as MD-700 (Taisho Pharmaceutical Co. Ltd) and LY295427 (Eli Lilly). The hypolipidemic agent may be a cholesterol absorption inhibitor preferably Schering-Plough's SCH48461 (ezetimibe) as well as those disclosed in *Atherosclerosis* 115, 45-63 (1995) and *J. Med. Chem.* 41, 973 (1998).

The other lipid agent or lipid-modulating agent may be a cholesteryl transfer protein inhibitor (CETP) such as Pfizer's CP-529,414 as well as those disclosed in WO/0038722 and in EP 818448 (Bayer) and EP 992496, and Pharmacia's SC-744 and SC-795, as well as CETi-1 and JTT-705.

The hypolipidemic agent may be an ileal $Na^+$/bile acid cotransporter inhibitor such as disclosed in Drugs of the Future, 24, 425-430 (1999). The ATP citrate lyase inhibitor which may be employed in the combination of the invention may include, for example, those disclosed in U.S. Pat. No. 5,447,954.

The other lipid agent also includes a phytoestrogen compound such as disclosed in WO 00/30665 including isolated soy bean protein, soy protein concentrate or soy flour as well as an isoflavone such as genistein, daidzein, glycitein or equol, or phytosterols, phytostanol or tocotrienol as disclosed in WO 2000/015201; a beta-lactam cholesterol absorption inhibitor such as disclosed in EP 675714; an HDL upregulator such as an LXR agonist, a PPAR α-agonist and/or an FXR agonist; an LDL catabolism promoter such as disclosed in EP 1022272; a sodium-proton exchange inhibitor such as disclosed in DE 19622222; an LDL-receptor inducer or a steroidal glycoside such as disclosed in U.S. Pat. No. 5,698,527 and GB 2304106; an anti-oxidant such as beta-carotene, ascorbic acid, α-tocopherol or retinol as disclosed in WO 94/15592 as well as Vitamin C and an antihomocysteine agent such as folic acid, a folate, Vitamin B6, Vitamin B12 and Vitamin E; isoniazid as disclosed in WO 97/35576; a cholesterol absorption inhibitor, an HMG-CoA synthase inhibitor, or a lanosterol demethylase inhibitor as disclosed in WO 97/48701; a PPAR δ agonist for treating dyslipidemia; or a sterol regulating element binding protein-I (SREBP-1) as disclosed in WO 2000/050574, for example, a sphingolipid, such as ceramide, or neutral sphingomyelenase (N-SMase) or fragment thereof. Preferred hypolipidemic agents are pravastatin, lovastatin, simvastatin, atorvastatin, fluvastatin, pitavastatin and rosuvastatin, as well as niacin and/or cholestagel.

The compounds of the present invention may be employed in combination with anti-hypertensive agents. Examples of suitable anti-hypertensive agents for use in combination with the compounds of the present invention include beta adrenergic blockers, calcium channel blockers (L-type and/or T-type; e.g. diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetamide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan and compounds disclosed in U.S. Pat. Nos. 5,612,359 and 6,043, 265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

Cannbinoid receptor modulators could be useful in treating other diseases associated with obesity, including sleep disorders. Therefore, the compounds described in the present invention could be used in combination with therapeutics for treating sleep disorders. Examples of suitable therapies for treatment of sleeping disorders for use in combination with the compounds of the present invention include melatonin analogs, melatonin receptor antagonists, ML 1 B agonists, GABA receptor modulators; NMDA receptor modulators, histamine-3 (H3) receptor modulators, dopamine agonists and orexin receptor modulators.

Cannabinoid receptor modulators may reduce or ameliorate substance abuse or addictive disorders. Therefore, combination of cannabinoid receptor modulators with agents used to treat addictive disorders may reduce the dose requirement or improve the efficacy of current addictive disorder therapeutics. Examples of agents used to treat substance abuse or addictive disorders are: selective serotonin reuptake inhibitors (SSRI), methadone, buprenorphine, nicotine and bupropion.

Cannabinoid receptor modulators may reduce anxiety or depression; therefore, the compounds described in this application may be used in combination with anti-anxiety agents or antidepressants. Examples of suitable anti-anxiety agents for use in combination with the compounds of the present invention include benzodiazepines (e.g., diazepam, lorazepam, oxazepam, alprazolam, chlordiazepoxide, clonazepam, chlorazepate, halazepam and prazepam), 5HT1A receptor agonists (e.g., buspirone, flesinoxan, gepirone and ipsapirone), and corticotropin releasing factor (CRF) antagonists.

Examples of suitable classes of anti-depressants for use in combination with the compounds of the present invention include norepinephrine reuptake inhibitors (tertiary and secondary amine tricyclics), selective serotonin reuptake inhibitors (SSRIs) (fluoxetine, fluvoxamine, paroxetine and sertraline), monoamine oxidase inhibitors (MAOIs) (isocarboxazid, phenelzine, tranylcypromine, selegiline), reversible inhibitors of monoamine oxidase (RIMAs) (moclobemide), serotonin and norepinephrine reuptake inhibitors (SNRIs) (venlafaxine), corticotropin releasing factor (CRF) receptor antagonists, alpah-adrenoreceptor antagonists, and atypical antidepressants (bupropion, lithium, nefazodone, trazodone and viloxazine).

The combination of a conventional antipsychotic drug with a CB-1 receptor antagonist could also enhance symptom reduction in the treatment of psychosis or mania. Further, such a combination could enable rapid symptom reduction, reducing the need for chronic treatment with antipsychotic agents. Such a combination could also reduce the effective antipsychotic dose requirement, resulting in reduced probability of developing the motor dysfunction typical of chronic antipsychotic treatment.

Examples of suitable antipsychotic agents for use in combination with the compounds of the present invention include the phenothiazine (chlorpromazine, mesoridazine, thioridazine, acetophenazine, fluphenazine, perphenazine and trifluoperazine), thioxanthine (chlorprothixene, thiothixene), heterocyclic dibenzazepine (clozapine, olanzepine and aripiprazole), butyrophenone (haloperidol), dipheyylbutylpiperidine (pimozide) and indolone (molindolone) classes of antipsychotic agents. Other antipsychotic agents with potential therapeutic value in combination with the compounds in the present invention include loxapine, sulpiride and risperidone.

Combination of the compounds in the present invention with conventional antipsychotic drugs could also provide an enhanced therapeutic effect for the treatment of schizophrenic disorders, as described above for manic disorders. As used here, schizophrenic disorders include paranoid, disorganized, catatonic, undifferentiated and residual schizophrenia, schizophreniform disorder, shcizoaffective disorder, delusional disorder, brief psychotic disorder and psychotic disorder not specified. Examples of suitable antipsychotic drugs for combination with the compounds in the present invention include the antipsychotics mentioned above, as well as dopamine receptor antagonists, muscarinic receptor agonists, 5HT2A receptor antagonists and 5HT2A/dopamine receptor antagonists or partial agonists (e.g., olanzepine, aripiprazole, risperidone, ziprasidone).

The compounds described in the present invention could be used to enhance the effects of cognition-enhancing agents, such as acetylcholinesterase inhibitors (e.g., tacrine), muscarinic receptor-1 agonists (e.g., milameline), nicotinic agonists, glutamic acid receptor (AMPA and NMDA) modulators, and nootropic agents (e.g., piracetam, levetiracetam). Examples of suitable therapies for treatment of Alzheimer's disease and cognitive disorders for use in combination with the compounds of the present invention include donepezil, tacrine, revastigraine, 5HT6, gamma secretase inhibitors, beta secretase inhibitors, SK channel blockers, Maxi-K blockers, and KCNQs blockers.

The compounds described in the present invention could be used to enhance the effects of agents used in the treatment of Parkinson's Disease. Examples of agents used to treat Parkinson's Disease include: levadopa with or without a COMT inhibitor, antiglutamatergic drugs (amantadine, riluzole), alpha-2 adrenergic antagonists such as idazoxan, opiate antagonists, such as naltrexone, other dopamine agonists or transportor modulators, such as ropinirole, or pramipexole or neurotrophic factors such as glial derived neurotrophic factor (GDNF).

The compounds described in the present invention could be used in combination with suitable anti-inflammatory agents. Examples of suitable anti-inflammatory agents for use in combination with the compounds of the present invention include prednisone, dexamethasone, cyclooxygenase inhibitors (i.e., COX-1 and/or COX-2 inhibitors such as NSAIDs, aspirin, indomethacin, ibuprofen, piroxicam, Naproxen®, Celebrex®, Vioxx®), CTLA4-Ig agonists/antagonists, CD40 ligand antagonists, IMPDH inhibitors, such as mycophenolate (CellCept®), integrin antagonists, alpha-4 beta-7 integrin antagonists, cell adhesion inhibitors, interferon gamma antagonists, ICAM-1, tumor necrosis factor (TNF) antagonists (e.g., infliximab, OR1384, including TNF-alpha inhibitors, such as tenidap, anti-TNF antibodies or soluble TNF receptor such as etanercept (Enbrel®), rapamycin (sirolimus or Rapamune) and leflunomide (Arava)), prostaglandin synthesis inhibitors, budesonide, clofazimine, CNI-1493, CD4 antagonists (e.g., priliximab), p38 mitogen-activated protein kinase inhibitors, protein tyrosine kinase (PTK) inhibitors, IKK inhibitors, and therapies for the treatment of irritable bowel syndrome (e.g., Zelnorm® and Maxi-K® openers such as those disclosed in U.S. Pat. No. 6,184,231 B1).

Exemplary of such other therapeutic agents which may be used in combination with cannabinoid receptor modulators include the following: cyclosporins (e.g., cyclosporin A), anti-IL-2 receptor (Anti-Tac), anti-CD45RB, anti-CD2, anti-CD3 (OKT-3), anti-CD4, anti-CD80, anti-CD86, monoclonal antibody OKT3, agents blocking the interaction between CD40 and gp39, such as antibodies specific for CD40 and/or gp39 (i.e., CD 154), fusion proteins constructed from CD40 and gp39 (CD40Ig and CD8gp39), inhibitors, such as nuclear translocation inhibitors, of NF-kappa B function, such as deoxyspergualin (DSG), gold compounds, antiproliferative agents such as methotrexate, FK506 (tacrolimus, Prograf), mycophenolate mofetil, cytotoxic drugs such as azathiprine and cyclophosphamide, anticytokines such as antiIL-4 or IL-4 receptor fusion proteins and PDE 4 inhibitors such as Ariflo, and the PTK inhibitors disclosed in the following U.S. patent applications, incorporated herein by reference in their entirety: Ser. No. 09/097,338, filed Jun. 15, 1998; Ser. No. 09/094,797, filed Jun. 15, 1998; Ser. No. 09/173,413, filed Oct. 15, 1998; and Ser. No. 09/262,525, filed Mar. 4, 1999. See also the following documents and references cited therein and incorporated herein by reference: Hollenbaugh, D., et al., "Cleavable CD40Ig Fusion Proteins and the Binding to Sgp39", *J. Immunol. Methods* (Netherlands), 188 (1), pp. 1-7 (Dec. 15, 1995); Hollenbaugh, D., et al., "The Human T Cell Antigen Gp39, A Member of the TNF Gene Family, Is a Ligand for the CD40 Receptor: Expression of a Soluble Form of Gp39 with B Cell Co-Stimulatory Activity", *EMBO J.* (England), 11 (12), pp. 4313-4321 (December 1992); and Moreland, L. W. et al., "Treatment of Rheumatoid Arthritis with a Recombinant Human Tumor Necrosis Factor Receptor (P75)-Fc Fusion Protein," *New England J. of Medicine*, 337 (3), pp. 141-147 (1997).

The above other therapeutic agents, when employed in combination with the compounds of the present invention, may be used, for example, in those amounts indicated in the Physicians' Desk Reference (PDR) or as otherwise determined by one of ordinary skill in the art.

The compounds of formula (I) of the invention can be administered orally or parenterally, such as subcutaneously or intravenously, as well as by nasal application, rectally or sublingually to various mammalian species known to be subject to such maladies, e.g., humans, in an effective amount up to 1 gram, preferably up to 200 mg, more preferably to 50 mg in a regimen of single, two or four divided daily doses.

The compounds of the formula (I) can be administered for any of the uses described herein by any suitable means, for example, orally, such as in the form of tablets, capsules, granules or powders; sublingually; bucally; parenterally, such as by subcutaneous, intravenous, intramuscular, or intrasternal injection or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories; in dosage unit formulations containing non-toxic, pharmaceutically acceptable vehicles or diluents. The present compounds can, for example, be administered in a form suitable for immediate release or extended release. Immediate release or extended release can be achieved by the use of suitable pharmaceutical compositions comprising the present compounds, or, particularly in the case of extended release, by the use of devices such as subcutaneous implants or osmotic pumps. The present compounds can also be administered liposomally.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate and/or lactose and/or other excipients, binders, extenders, disintegrants, diluents and lubricants such as those known in the art. The compounds of formula (I) can also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g. Carbopol 934). Lubricants, glidants, flavors, coloring agents and stabilizers may also be added for ease of fabrication and use.

Exemplary compositions for nasal aerosol or inhalation administration include solutions in saline which can contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor.

Exemplary compositions for rectal administration include suppositories which can contain, for example, a suitable non-irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as Plastibase (mineral oil gelled with polyethylene).

It will be understood that the specific dose level and frequency of dosage for any particular subject can be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition.

It should be understood that while this invention has been described herein in terms of specific embodiments set forth in detail, such embodiments are presented by way of illustration of the general principles of the invention, and the invention is not necessarily limited thereto. Certain modifications and variations in any given material, process step or chemical formula will be readily apparent to those skilled in the art without departing from the true spirit and scope of the present invention, and all such modifications and variations should be considered within the scope of the claims that follow.

What is claimed is:
1. A compound according to Formula I

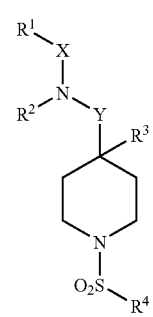

and pharmaceutically acceptable salts and stereoisomers thereof, wherein:
X is selected from the group consisting of —C(O)— and —S(O)$_2$—;
Y is —CH$_2$—;
R$^1$ is alkyl;
R$^2$ is selected from the group consisting of phenylalkyl and phenylalkenyl each of which is optionally substituted by halo or alkoxy;
R$^3$ is hydrogen; and
R$^4$ is selected from the group consisting of cyclohexyl, phenyl, and naphthyl, wherein
(i) the phenyl and naphthyl are each mono- or di- substituted; and
(ii) R$^4$ is
substituted at the 2, the 3 or the 2 and 3 position when R$^4$ is phenyl; and
wherein the substitutents for each of R$^1$ and R$^4$ are independently selected from the group consisting of hydrogen, halo, cyano, nitro, alkyl, alkenyl, CO$_2$alkyl, alkoxy, phenyl, phenoxy, trifluoromethoxy and CF$_3$.

2. A compound according to claim 1, wherein:
X is —C(O)—.

3. A compound according to claim 1, wherein:
R$^4$ is selected from the group consisting of phenyl and naphthyl, wherein the phenyl and naphthyl are each mono- or di- substituted.

4. A compound according to claim 3, wherein:
R$^4$ is substituted phenyl.

5. A pharmaceutical composition, comprising:
a compound according to claim 1 and a pharmaceutically acceptable diluent or carrier.

6. A pharmaceutical composition, comprising:
a compound according to claim 1; another therapeutic agent; and a pharmaceutically acceptable diluent or carrier.

7. A compound according to claim 1, wherein:
X is SO$_2$, R$^1$ is methyl and R$^2$ is 2-methyl-3-phenyl-2-(E)-propenyl.

8. A compound according to claim 1 wherein X=—C(O)— and R$^1$=cyclohexyl.

9. A compound according to claim 8 wherein R$^2$=phenylCH=C(CH$_3$)CH$_2$—.

10. A compound according to claim 1 wherein R$^4$ is selected from the group consisting of 2-fluorophenyl, 2-chlorophenyl, 2-bromophenyl, 2-methylphenyl, 3-fluorophenyl, 3-chlorophenyl, 3-bromophenyl, 3-trifluoromethoxyphenyl, 3-methoxyphenyl, 3-methylphenyl, 3-phenylphenyl, 3-phenoxyphenyl, 3-carbomethoxyphenyl, 3-nitrophenyl, 2,3-dichlorophenyl, and 2-methyl-3-chlorophenyl.

11. A compound according to claim 1 selected from the group consisting of Formula I wherein X=C(O), Y=—$CH_2$— $R^1$ =cyclohexyl, $R^2$=phenylCH=C($CH_3$)$CH_2$, $R^3$=H, and $R^4$ is
 a) 2-fluorophenyl or
 b) 2-chlorophenyl or
 c) 2-bromophenyl or
 d) 2-methylphenyl or
 e) 3-fluorophenyl or
 f) 3-chlorophenyl or
 g) 3-bromophenyl or
 h) 3-trifluoromethoxyphenyl or
 i) 3-methoxyphenyl or
 j) 3-methylphenyl or
 k) 3-phenylphenyl or
 l) 3-phenoxyphenyl or
 m) 3-carbomethoxyphenyl or
 n) 3-nitrophenyl or
 p) 2,3-dichlorophenyl or
 q) 2-methyl-3-chlorophenyl.

* * * * *

UNITED STATES PATENT AND TRADEMARK OFFICE
CERTIFICATE OF CORRECTION

PATENT NO. : 7,517,991 B2  Page 1 of 1
APPLICATION NO. : 11/247492
DATED : April 14, 2009
INVENTOR(S) : Sher et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 549 days.

Signed and Sealed this

Sixteenth Day of November, 2010

David J. Kappos
*Director of the United States Patent and Trademark Office*

UNITED STATES PATENT AND TRADEMARK OFFICE
CERTIFICATE OF CORRECTION

PATENT NO. : 7,517,991 B2  Page 1 of 1
APPLICATION NO. : 11/247492
DATED : April 14, 2009
INVENTOR(S) : Philip M. Sher et al.

It is certified that error appears in the above-identified patent and that said Letters Patent is hereby corrected as shown below:

On the Title Page:

Item (56), References Cited, under OTHER PUBLICATIONS:

Column 2, Dorwald reference, change "Wienheim" to -- Weinheim --.

The reference should read:

-- F.Z. Dorwald "Side Reactions in Organic Synthesis: A Guide to Successful Synthesis Design" 2005, Wiley-VCH Verlag GmbH & KGaA, Weinheim.* --.

Claim 11:

Column 41, line 4, change "X=C(O)" to -- X = -C(O)- --.

Column 41, line 5, change "Y=-CH$_2$-" to -- Y = -CH$_2$-, --.

Signed and Sealed this
Second Day of August, 2011

David J. Kappos
*Director of the United States Patent and Trademark Office*